US012797508B2

(12) United States Patent
Jeyapalina et al.

(10) Patent No.: US 12,797,508 B2
(45) Date of Patent: Nov. 17, 2026

(54) FLUORAPATITE-CONTAINING STRUCTURES

(71) Applicant: UNIVERSITY OF UTAH RESEARCH FOUNDATION, Salt Lake City, UT (US)

(72) Inventors: Sujeevini Jeyapalina, Salt Lake City, UT (US); Brian T. Bennett, Salt Lake City, UT (US); Jayant P. Agarwal, Salt Lake City, UT (US); Taylor David Sparks, Salt Lake City, UT (US); James Peter Beck, Salt Lake City, UT (US); Jill E. Shea, Salt Lake City, UT (US); Pratima Labroo, Salt Lake City, UT (US); Clark Nielson, Salt Lake City, UT (US); Prasenjit Podder, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 897 days.

(21) Appl. No.: 17/420,589

(22) PCT Filed: Jan. 9, 2020

(86) PCT No.: PCT/US2020/012950

§ 371 (c)(1),
(2) Date: Jul. 2, 2021

(87) PCT Pub. No.: WO2020/146646

PCT Pub. Date: Jul. 16, 2020

(65) Prior Publication Data

US 2022/0080079 A1 Mar. 17, 2022

Related U.S. Application Data

(60) Provisional application No. 62/790,685, filed on Jan. 10, 2019.

(51) Int. Cl.
*A61L 27/12* (2006.01)
*A61L 27/36* (2006.01)
*A61L 27/56* (2006.01)

(52) U.S. Cl.
CPC ........... *A61L 27/12* (2013.01); *A61L 27/3608* (2013.01); *A61L 27/3683* (2013.01); *A61L 27/56* (2013.01); *A61L 2430/02* (2013.01)

(58) Field of Classification Search
CPC ................ A61F 2/28; A61F 2002/2817; A61F 2002/2835; A61F 2310/00293; A61L 2430/02; A61L 27/12; A61L 27/3608; A61L 27/3683; A61L 27/56; C04B 2235/3212; C04B 2235/445; C04B 2235/5436; C04B 2235/963; C04B 35/447
See application file for complete search history.

(56) References Cited

U.S. PATENT DOCUMENTS

| | | | | |
|---|---|---|---|---|
| 6,136,029 | A | 10/2000 | Johnson et al. | |
| 8,916,228 | B2 | 12/2014 | Oh et al. | |
| 9,125,967 | B2 | 9/2015 | Denry et al. | |
| 2002/0187104 | A1* | 12/2002 | Li | A61L 24/108 424/44 |
| 2005/0260269 | A1 | 11/2005 | Engelbrecht et al. | |
| 2008/0069852 | A1 | 3/2008 | Shimp et al. | |
| 2008/0306554 | A1 | 12/2008 | Mckinley | |
| 2011/0081396 | A1 | 4/2011 | Denry | |
| 2011/0217356 | A1* | 9/2011 | Van Dyke | A61L 15/44 424/443 |
| 2012/0087954 | A1 | 4/2012 | Xia et al. | |
| 2012/0141599 | A1 | 6/2012 | Johns et al. | |
| 2012/0319316 | A1 | 12/2012 | Stephan | |
| 2014/0271565 | A1 | 9/2014 | Denry et al. | |
| 2018/0280570 | A1 | 10/2018 | Poundarik et al. | |
| 2022/0105241 | A1* | 4/2022 | Jeyapalina | A61L 27/06 |

FOREIGN PATENT DOCUMENTS

| | | | |
|---|---|---|---|
| CN | 101856511 | A | 10/2010 |
| CN | 101927993 | A | 12/2010 |
| CN | 102429745 | A | 5/2012 |
| CN | 103463681 | B | 1/2015 |
| CN | 109529107 | A | 3/2019 |
| DE | 4303575 | C1 | 4/1994 |
| EP | 2192876 | B1 | 3/2014 |
| JP | 2007098054 | A | 4/2007 |
| WO | 9423944 | A1 | 10/1994 |
| WO | 2011031821 | A1 | 3/2011 |
| WO | 2022146646 | A1 | 7/2022 |

OTHER PUBLICATIONS

Ayed et al.; "Pressureless sintering of fluorapatite under oxygen atmosphere"; J. Eur. Cer. Soc.; 20: 1069-1076. Published in 2000.*
International Search Report and Written Opinion from International Application No. PCT/US2020/012888 mailed May 19, 2020.
International Search Report and Written Opinion from International Application No. PCT/US2020/012950 mailed May 15, 2020.
U.S. Appl. No. 62/790,642, filed Jan. 10, 2019.
U.S. Appl. No. 62/790,685, filed Jan. 10, 2019.
Bennett, et al., "Characterization and evalution of fluoridated apatites for the development of infection-free percutaneous devices", Materials Science & Engineering C, 100, 2019, pp. 665-675.
Bhasin, et al., "Trends in prosthetic biomaterials in implants dentistry", Prosthetic biomaterials in dental implantology, Journal of the International Clinical Dental Research Organization, Supplement 1, vol. 7, 2015, pp. S148- S160.

(Continued)

*Primary Examiner* — Jeffrey T. Palenik
(74) *Attorney, Agent, or Firm* — Workman Nydegger

(57) ABSTRACT

Embodiments disclosed herein relate scaffolds containing fluoridated apatites sintered at a temperature of at least 950° C. to increase integration of the scaffold in a patient, as well as methods of making and using the same.

16 Claims, 15 Drawing Sheets

Specification includes a Sequence Listing.

(56) References Cited

OTHER PUBLICATIONS

Kim, et al., "Porous ZrO2 bone scaffold coated with hydroxyapatite with fluorapatite intermediate layer", Science Direct, Biomaterials 24, 2003, pp. 3277-3284.
Lew, et al., "Macroporous bioceramics: A remarkable material for bone regeneration", Journal of Biomaterials Applications, 27(3), 2011, pp. 345-358.
Overgaard, et al., "Hydroxyapatite and Fluorapatite Coatings for Fixation of Weight Loaded Implants", Clinical Orthopaedics and Related Research, No. 336, Mar. 1997, pp. 286-296.
Seyedmajidi, et al., "Evaluation of antibacterial properties of hydroxyapatite/bioactive glass and fluorapatite/bioactive glass nanocomposite foams as a cellular scaffold of bone tissue", Journal of Laboratory Physicians, vol. 10, Issue 3, Jul.-Sep. 2018, pp. 265-271.
International Search Report and Written Opinion from International Application No. PCT/US2022/042181 mailed Dec. 19, 2022.
U.S. Appl. No. 17/420,579, filed Jul. 2, 2021.
U.S. Appl. No. 17/420,589, filed Jul. 2, 2021.
U.S. Appl. No. 63/239,749, filed Sep. 1, 2021.
U.S. Appl. No. 63/300,742, filed Jan. 19, 2022.
Abdolahi , et al., "Evaluation of Mechanical Properties and Apatite Formation of Synthesized Fluroapatite-Hardystonite Nanocomposite Scaffolds", Advanced Ceramic Progress, 2018, pp. 8-15.
Balasubramanian , et al., "Zinc-containing bioactive glasses for bone regeneration, dental and orthopedic applications", Biomed. Glasses, May 2015, pp. 51-69.
Gross , et al., "Efficient zinc incorporation into hydroxyapatite through crystallization of an amorphous phase could extend the properties of zinc apatites", Journal of the Australian Ceramic Society, 2013, pp. 129-135.
Kim , et al., "Fluor-hydrosyapatite sol-gel coating on titanium substrate for hard tissue implants", Science Direct Biomaterial 25, 2004, pp. 3351-3358.
Nasiri-Tabrizi , et al., "Mechanochemical Synthesis of Fluorapatite-Zinc Oxide (FAp-ZnO) Composite Nanopowders", Progress in Natural Science, Jul. 2012, pp. 340-349.
Nielson , et al., "Substituted Apatites as Regenerative Bone Scaffolds", Society for Biomaterials, 2021 Annual Meeting, Abstract 349, 2021, 1 page.
Pajor , et al., "Hydroxyapatite and Fluorapatite in Conservative Dentistry and Oral Implantology—A Review", Materials, Aug. 2019, 16 pages.
Uysal , et al., "Co-doping of hydroxyapatite with zinc and fluoride improves mechanical and biological properties of hydroxyapatite", Progress in Natural Science, Aug. 2014, pp. 340-349.
Xiao , et al., "Environment-Friendly Synthesis of Trace Element Zn, Sr, and F Codoping Hydroxyapatite with Non-cytotoxicity and Improved Osteoblast Proliferation and Differentiation", Biological Trace Element Research, 185, Jan. 18, 2018, pp. 148-161.
Fahami et al.; Synthesis, bioactivity and zeta potential investigations of chlorine and fluorine substituted hydroxyapatite; Elsevier; Materials Science and Engineering C 59 (2016) 78-85. (Year: 2016).
Wikipedia.com Demineralized Bone Matrix Dec. 23, 2018.

* cited by examiner

SEQUENCE LISTING

```
<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: Forward primer for targeting GAPDH

<400> SEQUENCE: 1

accaccatgg agaaggc                                                     17


<210> SEQ ID NO 2
<211> LENGTH: 20
<212> TYPE: DNA
<213> ORGANISM: Artificial Sequence
<220> FEATURE:
<223> OTHER INFORMATION: Reverse primer for targeting GAPDH

<400> SEQUENCE: 2

ggcatggact gtggtcatga                                                  20


<210> SEQ ID NO 3
<211> LENGTH: 21
<212> TYPE: DNA
<213> ORGANISM: Artificial Sequence
<220> FEATURE:
<223> OTHER INFORMATION: Forward primer for targeting osteocalcin

<400> SEQUENCE: 3

aagcccagcg actctgagtc t                                                21


<210> SEQ ID NO 4
<211> LENGTH: 21
<212> TYPE: DNA
<213> ORGANISM: Artificial Sequence
<220> FEATURE:
<223> OTHER INFORMATION: Reverse primer for targeting osteocalcin

<400> SEQUENCE: 4

aggtagcgcc ggagtctatt c                                                21


<210> SEQ ID NO 5
<211> LENGTH: 23
<212> TYPE: DNA
<213> ORGANISM: Artificial Sequence
<220> FEATURE:
<223> OTHER INFORMATION: Forward primer for targeting SPP1

<400> SEQUENCE: 5

tggccgaggt gatagtgtgg tta                                              23


<210> SEQ ID NO 6
<211> LENGTH: 21
<212> TYPE: DNA
<213> ORGANISM: Artificial Sequence
```

-continued

```
<220> FEATURE:
<223> OTHER INFORMATION: Reverse primer for targeting SPP1

<400> SEQUENCE: 6

aacggggatg gccttgtatg c                                              21
```

FLUORAPATITE-CONTAINING STRUCTURES

CROSS-REFERENCE TO RELATED APPLICATIONS

This application is a U.S. National Stage Application of PCT International Patent Application No. PCT/US2020/012950 filed on 9 Jan. 2020, which claims priority to U.S. Patent Application No. 62/790,685 filed on 10 Jan. 2019, the disclosure of each of which is incorporated herein, in its entirety, by this reference.

STATEMENT REGARDING FEDERALLY SPONSORED RESEARCH

This invention was made with government support under Grant Number W81XWH-15-1-0682 (OR140116) awarded by the U.S. Department of Defense. The U.S. government has certain rights in the invention.

INCORPORATION BY REFERENCE OF SEQUENCE LISTING

This application includes a Sequence Listing submitted electronically in ASCII format. The ASCII copy of the Sequence Listing, created on Jun. 25, 2026, is named 6300-642-1a-1 SeqList.txt and is 1,577 bytes in size. The ASCII copy of the Sequence Listing is expressly incorporated herein by this reference.

BACKGROUND

Implantable scaffolds may be surgically implanted into tissue(s) of a subject, such as a human or animal. Implantable scaffolds often fail because the implant fails to integrate in the implantation site.

Long-term success of dental implants is dependent upon sustained osseointegration. Without sufficient bone to support the implant, loosening will occur, increasing the risk of biomechanical overload and/or implant fracture, which often require implant removal and re-implantation.

SUMMARY

Embodiments disclosed herein relate to scaffolds formed with fluoridated apatites to promote integration into patients as well as methods of making and using the same. In an embodiment, an implantable scaffold is disclosed. The implantable scaffold includes a fluoridated apatite structure sized and shaped for implantation in an animal. The fluoridated apatite structure exhibits a surface morphology and porosity consistent with having been sintered at about 950° C. or more.

In an embodiment, an method of making an implantable scaffold is disclosed. The method includes providing fluoridated apatite particles. The method includes sintering the fluoridated apatite particles at a sintering temperature of at least 950° C. to form a sintered body. The method includes forming the scaffold from the sintered body.

In an embodiment, a method of using a scaffold having fluoridated apatite is disclosed. The method includes providing a scaffold having fluoridated apatite exhibiting a surface morphology and porosity consistent with having been sintered at about 950° C. or more. The method includes implanting the scaffold in a subject.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

DETAILED DESCRIPTION

Figure 1:
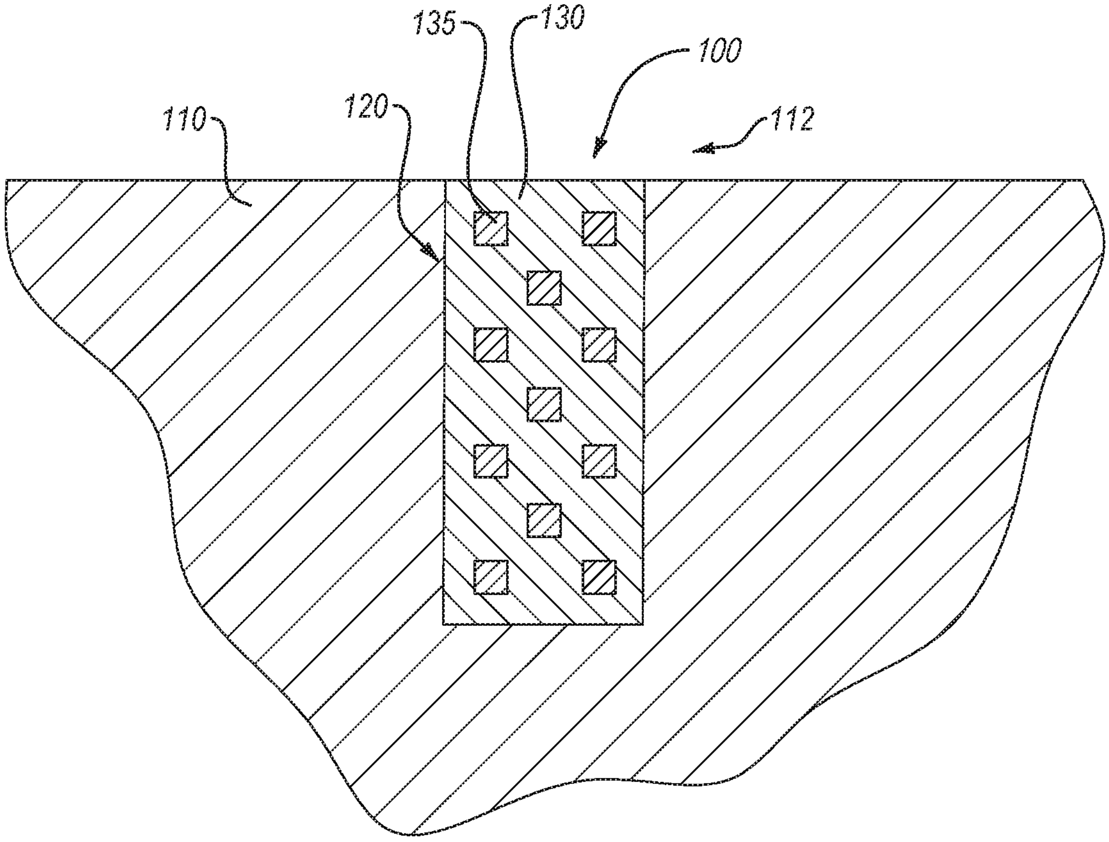
FIG. 1 is a side cross-sectional view of a scaffold disposed in a wound site, according to an embodiment.

Embodiments disclosed relate to scaffolds containing fluoridated apatites to improve osseointegration as well as methods of making and using the same. The scaffolds disclosed herein are tissue engineered bone substitutes for grafting of a diseased/damaged tissue and may include at least some of three major components, a mechanically compatible fluoridated apatite scaffold, a reliable source of osteogenic cells, and cytokine/growth factors (e.g., osteogenic signals).

The fluoridated apatites disclosed herein include one or more of fluorohydroxyapatite ("FHA") or fluorapatite ("FA") that is sintered at a sintering temperature selected to provide a desired surface morphology for the scaffold. FHA ($Ca_{10}(PO_4)_6\,F_y(OH)_{2-y}$) and FA ($Ca_{10}(PO_4)_6F_2$) are partially and fully fluoridated forms of apatite (e.g., Hydroxyapatite [$Ca_{10}(PO_4)_6(OH)_2$]), respectively. The fluoridated apatite scaffolds disclosed herein demonstrate excellent adhesion to tissue cells relative to implants or scaffolds formed from other materials such as hydroxyapatite. The scaffolds disclosed herein may be used as bone grafts, such as a bone substitute or carrier for the same. Proper integration of the bone with the implant surface is important for maintaining a stable interface and preserving implant integrity. Further, the scaffolds disclosed herein may include dopants composed to initiate and sustain bone growth and integration, such as an implantee's own stem cells (adipose derived stem cells (ASCs)), bone morphogenetic protein-2 (BMP-2), tissues, combinations thereof, or the like. A binder or other components may be present in the scaffold.

The bulk structure of the scaffolds herein are made of nonbiological materials (e.g., materials foreign to the body's internal environment such as FA) that may be used as bone implants. Conventional bone implants may include autografts or allografts. Autologous bone graft transplantation has no immunogenic response, but it has a limited supply. Decellularized allografts harvested from cadaveric sources have the advantage of being osteoconductive and osteogenic; however, they can be associated with risk of infectious disease immunogenicity, host rejection, and accelerated graft resorption. Allografts have no cells and require cells to migrate in, which takes time, during which time large grafts may resorb and lose strength and structure, which may cause failure of the allografts. Bone substitutes have been developed in response to the shortcomings of autografts and allografts. Bone substitutes have focused on providing the necessary matrix to support bone regeneration by providing a biocompatible, bioresorbable, and porous scaffold made from materials such as hydroxyapatite, collagen, and biodegradable synthetic materials.

Conventional scaffolds that have integrated extracellular matrix proteins or growth factors, typically BMPs, have certain limitations, such as the uncontrolled release of growth factors, which leads to the formation of bone in undesirable areas of the body (e.g., ectopic bone formation). In contrast, the autograft-like living bone substitutes of the scaffolds disclosed herein may incorporate cell types that the patient's own body already utilizes in response to bone loss or physical insult. As the scaffold material (e.g., fluorapatite) is naturally resorbed within the body over time, it is replaced with new bone formation that may be stimulated within the porous structure by the addition of growth factors such as (e.g., BMP-2). Moreover, the use of fluorapatite structures results in a relatively slower resorption rate than in conventional bone implants, thereby mitigating the undesirable premature release of growth factors described above.

The scaffolds disclosed herein are sized and shaped for implantation in an animal (e.g., human) For example, the scaffolds disclosed herein can be custom fabricated to fit the precise size and shape of a defect a patient presents with. The scaffolds disclosed herein eliminate requirements for autograft donor sites, a second surgery to harvest grafts, pain associated with graft removal, and prolonged recovery time. The scaffolds disclosed herein may also be sterile, off-the-shelf products that may be opened in the operating room by the surgical team such as immediately prior to implantation.

Autograft-like porous bone scaffolds are described herein. They may be fabricated with a mineral matrix (e.g., fluoridated apatite scaffold), biologic factors, and the patient's own stem cells for de novo osseous tissue repair and regeneration. As the scaffold is naturally resorbed over time, it is replaced with an influx of new bone formation, due in part to the biological factors (e.g., dopants) released into the adjacent healthy bone. Accordingly, the scaffolds disclosed herein are particularly useful in the orthopaedic, plastic surgery, and dental fields as a customizable scaffold material to repair instances of bone loss, defects, and trauma.

FIG. 1 is a side cross-sectional view of a scaffold 100 disposed in a bone 110, according to an embodiment. The scaffold 100 may be disposed in the bone 110 or other tissue of a patient, such as at a wound site 112 (e.g., implantation site). The tissue may include one or more tissues, such as soft tissue (e.g., skin), hard tissue (e.g., bone), or combinations thereof. As shown, a pocket 120 extends into the bone 110 at the wound site 112. The pocket 120 may be formed by an injury or surgical intervention. For example, an area within a jaw bone may be cleared or shaped to make room for an implant, such as to build up bone for implantation of a dental implant. Similarly, space in a hip, a femur, spine, etc. may be formed receive a scaffold to replace damaged bone tissue. The scaffold 100 may be positioned within the wound site 112, such as in one or more of soft tissue or hard tissue (e.g., bone).

The scaffold 100 serves as a structure that provides mechanical strength, a substrate for bone growth, a delivery means for one or more dopants, and which eventually is resorbed in the body. The bulk structure of the scaffold 100 is formed of fluoridated apatite such as one or more of FA or FHA. The bulk structure of the scaffold 100 may be a porous sponge-like (though substantially rigid) structure. The bulk structure of the scaffold 100 may be framework, block, rod, plug, wedge, or any other structure formed from a plurality of fluoridated apatite particles and has a plurality of pores therein. The bulk structure of the scaffold may be shaped to fit into a selected space or cavity, within a subject's body. At least some of the pores in the bulk structure of the scaffold may be formed by casting fluoridated apatite material in an investment material and removing the investment material, such as by one or more of dissolution, combusting, heating, machining, lasing, or any other suitable technique. At least some of the pores in the scaffold 100 (e.g., in the microstructure) may be due to the crystalline nature of the fluoridated apatite of the scaffold 100.

The scaffold 100 defines a plurality of surfaces that can bond to bone or other tissues and may provide a substrate through which dopants may be delivered to the implantation site. The scaffold 100 may include one or more void spaces 130 therein. The void spaces 130 may be pores. In some embodiments, the void spaces 130 may include pores or chambers formed (e.g., molded, machined, dissolved, etc.) in the bulk structure of the scaffold 100.

The scaffold 100 may include one or more dopants 135. For example, one or more surfaces of the scaffold 100 may have the one or more dopants 135 disposed thereon. The one or more void spaces 130 may be filled with one or more dopants 135, such as dopants to promote bone growth. Suitable dopants 135 may include collagen, keratose, differentiation promoters (e.g., BMP-2), stem cells (e.g., ASCs), demineralized bone matrix, and the like.

The scaffold 100 may be formed in any shape (e.g., size and dimensions) for implantation into the tissues (e.g., hard and/or soft tissues) of a subject. For example, the scaffold 100 may be sized and shaped to form a post, a screw, a joint, a socket, a ball, or any other bone structure. In embodiments, the scaffold 100 may be disposed on or sized and shaped to host percutaneous implant such as percutaneous osseointegrated (OI) prosthetics, dental implants, orthopedic implants, or the like.

The fluoridated apatite in the scaffold 100 provides a medium for preferential attachment of tissue cells (e.g., osteoblast cells, epithelial cells, etc.) to the scaffold 100. The scaffold 100 includes fluoridated apatite material such as, FHA, FA, or combinations thereof. For example, the scaffold 100 may consist of or consist essentially of FA, FHA, one or more dopants 135, or combinations of any of the foregoing. In embodiments, the scaffold 100 may consist of or consist essentially of FA and one or more dopants. FA has proven to be particularly effective at adhering to the osteoblast cells. FA in the scaffold 100 promotes tissue adhesion which provides a substrate for new bone growth, and which reduces or eliminates downgrowth along the surfaces of the scaffold, thereby reducing or eliminating infections at the wound site 112 (e.g., implant site). The scaffolds disclosed herein increase tissue bonding and growth at the surface of the scaffold. The scaffolds disclosed herein reduce or eliminate downgrowth of osteoblast cells, epithelial cells, or other local cells along the scaffold surface relative to conventional scaffolds (e.g., scaffolds that do not have the fluoridated apatite structure disclosed herein). Osteoblast cells showed great affinity for fluoridated apatite surfaces that were sintered at 1050° C. to 1250° C. when compared to HA and titanium surfaces.

The material that forms the bulk structure of the scaffolds 100 disclosed herein includes fluoridated apatite that has been sintered at a temperature between about 950° C. and about 1,350° C., or more particularly between about 1,050° C. and about 1,250° C. The inventors currently believe that fluoridated apatite sintered in the temperature range(s) disclosed above agglomerate to form a plurality of bonded agglomerations of fluoridated apatite that have a size, shape, and zeta potential that encourage adhesion between tissue cells and the fluoridated apatite (e.g., FA) in the scaffold.

Figure 2A:
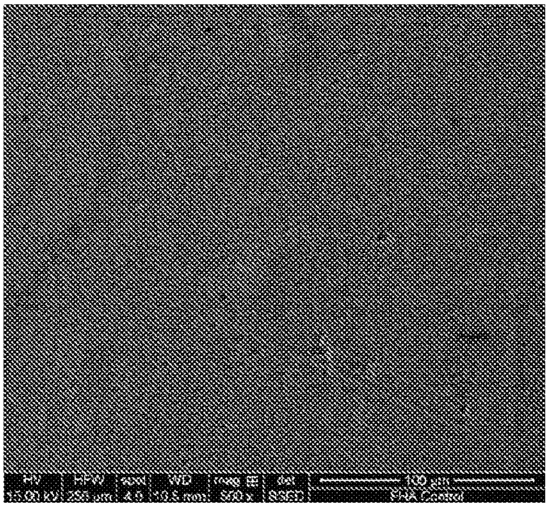
FIGS. 2A-2D are electron photomicrographs of fluorapatite before and after sintering at 1,200° C.
Figure 2B:
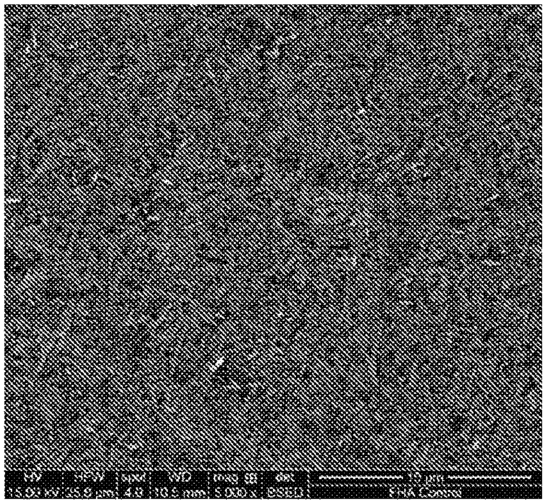

In an unsintered state, fluoridated apatite exhibits a substantially rod-like or needle-like crystal structure. During sintering, the individual fluoridated apatite crystals agglomerate and exhibit various bulk structures and surface morphologies. FIGS. 2A-2D are electron photomicrographs of FA before and after sintering at 1,200° C. FIG. 2A is an electron photomicrograph of unsintered FA shown in a first magnification (500×). As shown, the bulk structure of the unsintered FA appears to be a porous mass of particles. FIG. 2B is an electron photomicrograph of unsintered FA at a second magnification (5000×). As shown in FIG. 2B, the microstructure (e.g., each particle of the bulk structure) of the unsintered FA is rod-like or linear crystals.

Figure 2C:
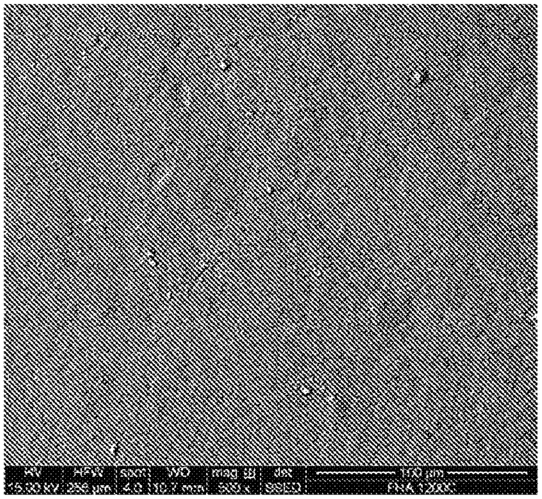
Figure 2D:
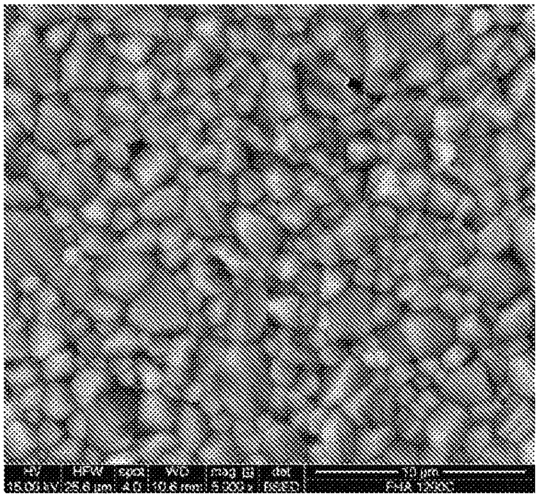

The FA particles of FIGS. 2A and 2B were sintered at 1,200° C. and examined at the same magnification as FIGS. 2A and 2B to produce FIGS. 2C and 2D. FIG. 2C is an electron photomicrograph of the sintered FA shown at the first magnification. As shown, the bulk structure of the sintered FA appears to be a porous mass of particles having a greater (average) particle size than the unsintered FA shown in FIG. 2A. FIG. 2D is an electron photomicrograph of sintered FA at the magnification (5000×). As shown, the microstructure (e.g., each particle of the bulk structure) of the unsintered FA appears to be substantially granular agglomerations with a far greater average particle size (e.g., volume) than the unsintered FA particles.

FIGS. 2A-2D demonstrate that unsintered FA particles may begin with rod-like or substantially linear structure having a width (smallest dimension) of less than about 1 μm, such as less than about 0.5 μm and a length that is less than about 4 μm or less than about 2 μm; and through sintering may be formed into agglomerates exhibiting greater three dimensional characteristics. For example, the as-sintered FA may be agglomerated into substantially granular shapes (e.g., prismatic, pseudo-prismatic, rounded, spherical, semi-spherical, ellipsoid, or irregularly rounded shapes). The as-sintered FA (or FHA) may be substantially devoid of the rod-like or needle-like fluoridated apatite of the unsintered FA (or FHA). The average volume of an average sintered FA agglomerate may be at least ten times the average volume of the average unsintered FA particle. The smallest dimension of the average agglomerate of sintered FA particles may be at least about 0.5 μm, such as about 0.5 μm to 10 μm, or about 1 μm to 5 μm. As shown in FIGS. 2A-2D, the surface morphology of the FA particles drastically changes as a result of sintering. The resulting sintered FA particles (e.g., agglomerates), exhibit an overall smoother surface morphology than the unsintered FA particles.

Bulk fluoridated apatite particles may be a coherent mass of agglomerations provided in a specific form, such as grains of the scaffold 100 (FIG. 1). Bulk fluoridated apatite particles may be formed by sintering a mass of fluoridated apatite particles and then grinding, crushing, or otherwise breaking the resulting sintered bulk body into smaller bulk particles. The smaller bulk particles may be sized, such as using a sieve, to provide a plurality of particles having a substantially homogenous average particle size. The bulk particle size (e.g., a coherent mass of agglomerations provided in a granular form) of the bulk fluoridated apatite particles disclosed herein may be at least about 5 μm, such as about 30 μm to 300 μm, about 60 μm to 200 μm, about 65 μm to 150 μm, about 60 μm to 120 μm, about 120 μm to 200 μm, or less than about 300 μm.

The porosity of a scaffold of the sintered FA particles is also different than the porosity of a scaffold of the unsintered FA particles. For example, the bulk structure of the sintered FA particles exhibits less porosity than the unsintered FA particles. This is believed to be due to the agglomerates densifying (e.g., self-organizing or building into naturally fitting structures) during sintering, thereby providing less pore space therebetween than the unsintered particles.

Figure 3A:
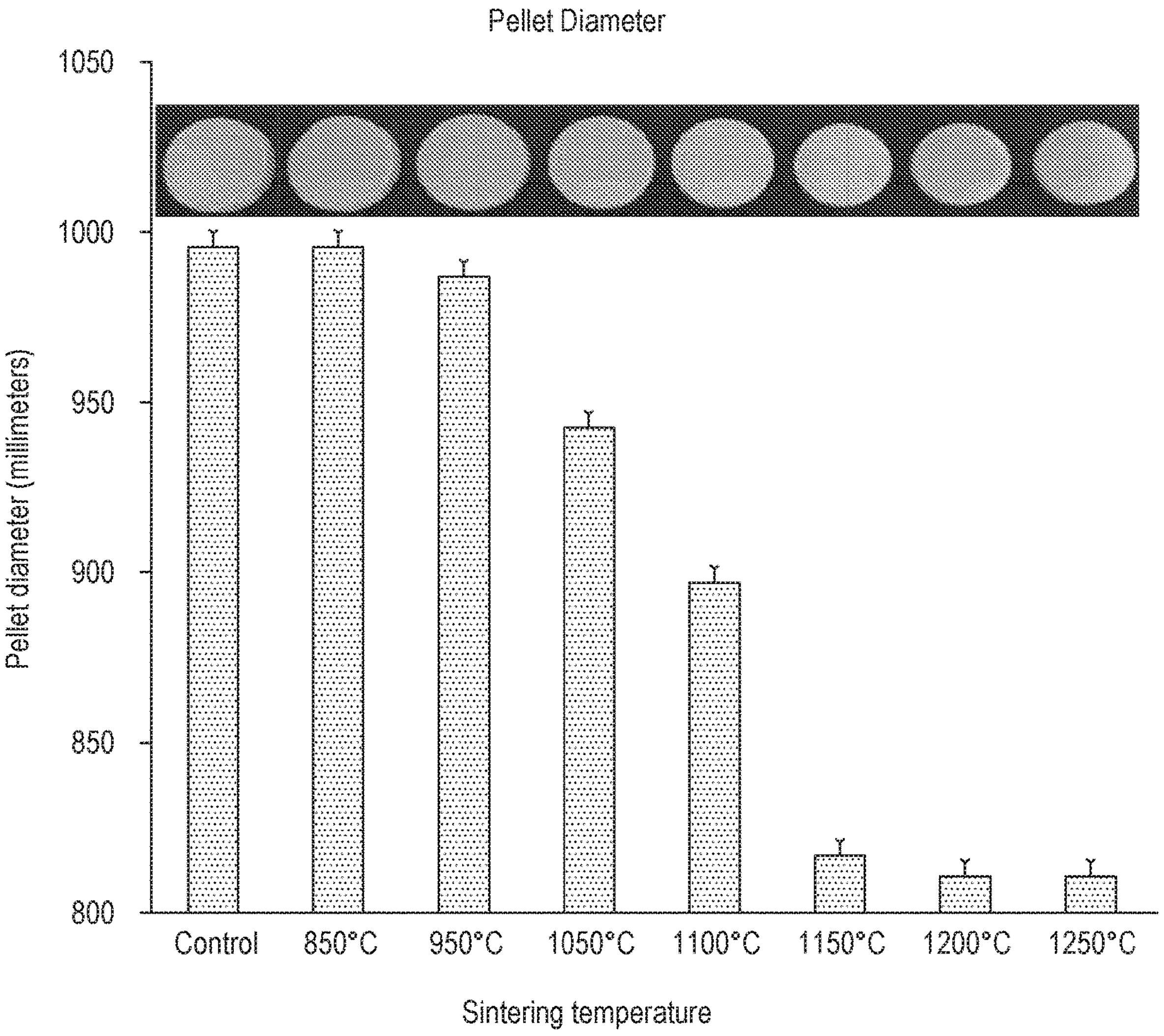
FIG. 3A is a bar graph of the pellet diameter of fluoridated pellets sintered at various temperatures.

FIG. 3A is a graph of the pellet diameter of fluoridated pellets sintered at various temperatures. As shown, pellets formed from fluoridated apatite and which have an initial diameter of about 10 mm show significant shrinkage at sintering temperatures between 1,050° C. and 1,250° C., particularly between 1,150° C. and 1,250° C. For example, fluoridated apatite pellets with an initial diameter of about 10 mm which were sintered at 1,150° C., 1,200° C., and 1250° C. respectively, exhibited nearly a 20% reduction in diameter (e.g., to about 8 mm). Notably, pellets sintered at 850° C. and 950° C. substantially retained their original size (about 10 mm). Thus, the fluoridated apatite is densified at temperatures between 1,050° C. and 1,250° C., particularly between 1,150° C. and 1,250° C.

Fluoridated apatite maintains a relatively strong mechanical strength, even after sintering. For example, fabricated heat-treated FA and FHA scaffolds, which showed enhanced osteoblast cellular adhesion and proliferation properties when compared to HA surfaces treated at the same temperatures, also showed compressive strengths of 100-200 MPa, which is similar to cortical bone (170-193 MPa cortical bone; 7-10 MPa cancellous bone).

The inventors currently believe that the porosity and surface morphology of the sintered FA particles increase adhesion to tissue cells (e.g., epithelial cells, osteoblasts, fibroblasts, etc.). The charge of the fluoridated apatite material also contributes to increased tissue adhesion. For example, the surface charge of the fluoridated apatite material is believed to increase differentiation of cells at the interface therebetween. The FA is more electronegative than FHA and HA. As shown below, experiments have demonstrated that sintered FA promotes adhesion to osteoblasts, and to a much higher degree than sintered FHA and HA.

The surface charge of the scaffold material may be measured as the zeta potential. In some cases, the zeta potential of FA is more than double the zeta potential of FHA or HA sintered under the same conditions. The zeta potential of the fluoridated apatite scaffolds disclosed herein may be less than (e.g., have a greater negative value than) about −10 mV, such as about −10 mV to −80 mV, about −20 mV to −65 mV, about −26 mV to −80 mV, about −26 mV to −65 mV, about −40 mV to −80 mV, less than about −26 mV, less than about −35 mV, or less than about −40 mV. The inventors currently believe that the electronegativity of the fluorine atoms in the fluoridated apatite drive the zeta potential lower and stimulate cell adhesion, such as by causing differentiation.

The scaffolds disclosed herein include fluoridated apatite that has been sintered at a temperature between about 950° C. and 1,350° C. (e.g., about 1,050° C. to 1,250° C., about 1,050° C. to 1,150° C., or about 1,150° C. to 1,250° C.), exhibits a surface morphology that is different from unsintered fluoridated apatite (e.g., includes agglomerations of particles), and has a zeta potential that is lower than −10 mV (e.g., less than −26 mV, less than −40 mV, or about −26 mV to −65 mV).

Zeta potential measurements were used to identify the electrical potential of the material surfaces (Table 1). These data showed that synthesized apatites, were negatively charged at physiological pH (e.g., 7.4). As shown in Table 1 below, sintering appeared to increase negative zeta potential values of the HA, FHA, and FA, the FA sintered at 1250° C. produced the most negatively charged surface.

Overall surface charges of synthesized apatites (HA, FHA, and FA) were quantified using zeta potential. Four samples of each species of apatite (HA, FHA, and FA) were provided. They included an unsintered sample, a sample sintered at 1,050° C., a sample sintered at 1,150° C., and a sample sintered at 1,250° C. The zeta potential of the samples was examined using a Massively Parallel Phase Analysis Light Scattering (MP-PALS) spectrometer (Mobius mobility instrument; Wyatt Technology Corp., Santa Barbara, CA). For the measurement, 100 mg of the various apatite samples (powders) were suspended in a 10 mL solution of 0.154M NaCl (pH 7.4) to acquire a concentration of 0.01 g/mL. Next, 100 μL of this suspension was placed into a cuvette. After waiting a minute for the larger particles to settle to the bottom, each sample was measured nine times. The zeta potential was reported as the average value±95% CI. Table 1 provides the results of the analysis of the zeta potential of various apatite samples, both sintered and unsintered.

TABLE 1

| Material Type | Zeta Potential (mV) |
|---|---|
| FA (unsintered) | −19.0 ± 1.7 |
| FA-sintered at 1050° C. | −15.0 ± 3.2 |
| FA-sintered at 1150° C. | −28.2 ± 9.1 |
| FA-sintered at 1250° C. | −60.4 ± 2.0 |
| FHA (unsintered) | −8.7 ± 2.9 |
| FHA-sintered at 1050° C. | −15.9 ± 5.3 |
| FHA-sintered at 1150° C. | −15.4 ± 4.0 |
| FHA-sintered at 1250° C. | −15.6 ± 5.2 |
| HA (unsintered) | −9.8 ± 2.3 |
| HA-sintered at 1050° C. | −16.1 ± 4.3 |
| HA-sintered at 1150° C. | −15.1 ± 5.1 |
| HA-sintered at 1250° C. | −24.2 ± 8.6 |

An experiment was carried out to determine the efficacy of using FA or FHA to bond to osteoblast cells and promote differentiation. A known number of osteoblast cells were seeded onto HA, FHA, and FA disks, respectively, and allowed to adhere and proliferate on the surface. At 48 hours post-seeding, cells were stripped with trypsin and numerated. These cells were then lysed, ribonucleic acid (RNA) was extracted, and quantitative polymerase chain reaction (qPCR) experiments were performed to examine gene expression of various osteogenic markers.

Figure 3B:
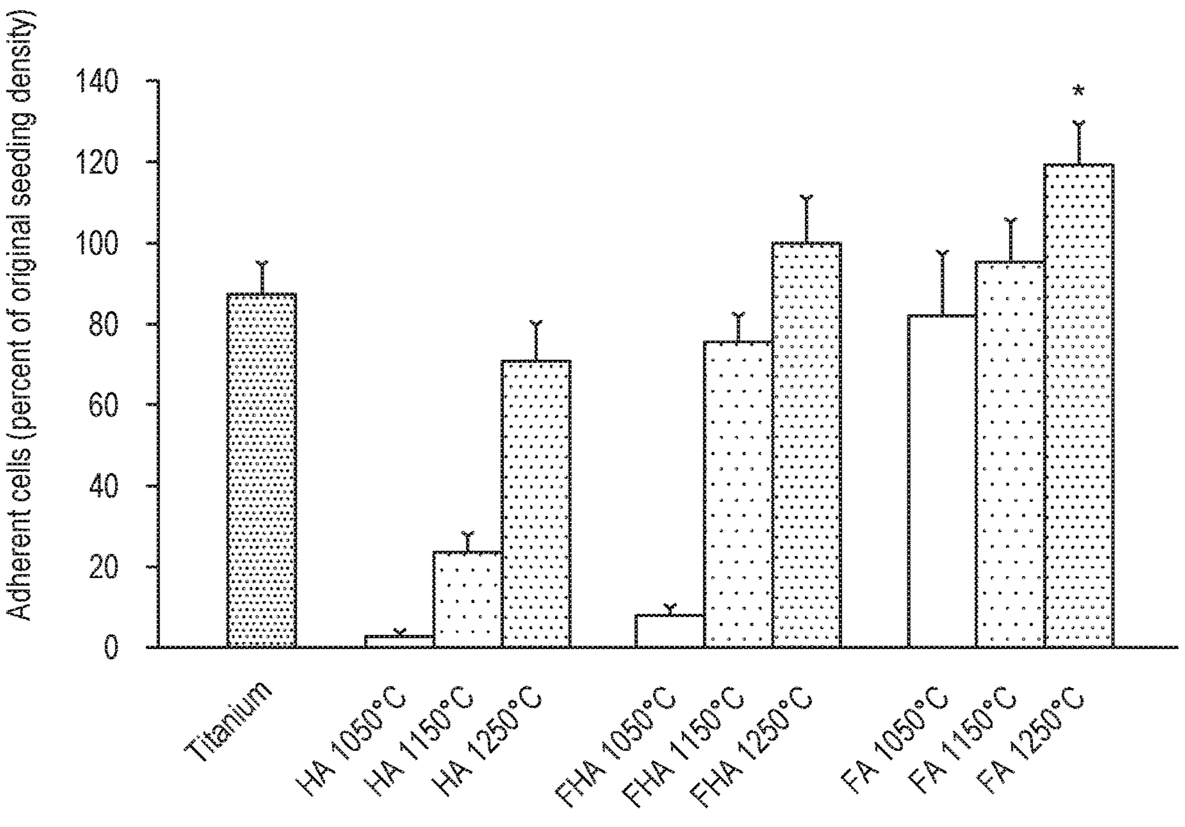
FIG. 3B is a bar chart of adhesion properties of various samples to osteoblasts.

FIG. 3B is a bar chart of adhesion properties of various samples to osteoblasts. As shown in FIG. 3B, the fluoridated apatite samples (FA and FHA) showed superior osteoblast cell adhesion properties compared to HA samples at each sintering temperature. The FA sample sintered at 1,250° C. showed marked improvement of cell adhesion over all other samples including the titanium control sample. Accordingly, the FA sample sintered at 1,250° C. was upregulated significantly beyond even the titanium control sample. As explained in more detail below, bone marrow stromal cells (BMSC) also exhibited greater adhesion in samples sintered at 1250° C.

As explained in more detail below, similar results were achieved for markers for positive osteogenic differentiation of various samples of matrix material. qPCR analysis of alkaline phosphatase (ALK Phos) and secreted phosphoprotein 1 (SPP1) genes as a marker for positive osteogenic differentiation was performed. SPP1 genes were significantly upregulated in FA sintered at 1,250° C. when compared to other tested materials, such as HA, FHA, and Ti. Further, FA showed more ALK Phos and SPP1 genes at all sintering temperatures (e.g., 1,050° C., 1,150° C., and 1,250° C.) than HA and FHA.

FA sintered at 1250° C. promoted adhesion, proliferation, and differentiation compared to titanium (Ti) and HA. Further, when compared to Ti and HA, osteoblasts seeded on the FA surfaces sintered at 1250° C. showed more than 20-fold and 13-fold gene overexpression of SPP1 (a marker for osteopontin, i.e., mineralized bone matrix marker), respectively.

Various techniques may be used to manufacture the scaffolds having fluoridated apatite particles and doped scaffolds as disclosed herein.

Figure 4:
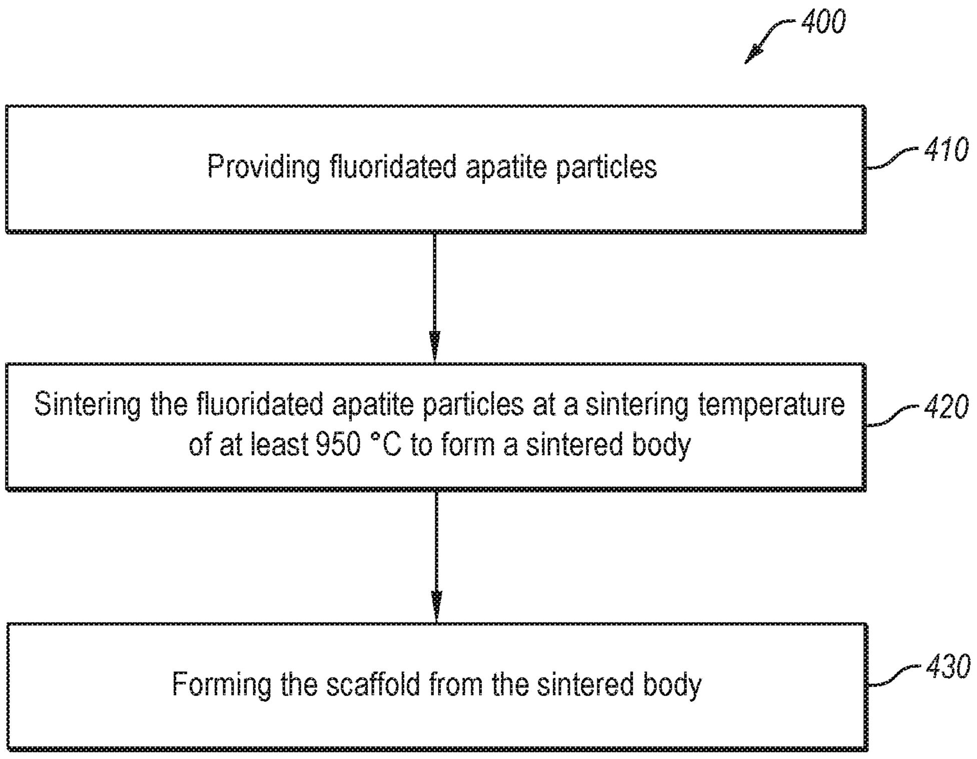
FIG. 4 is a flow diagram of a method of making an implantable scaffold, according to an embodiment.

FIG. 4 is a flow diagram of a method 400 of making a scaffold, according to an embodiment. The method 400 includes block 410 of providing fluoridated apatite particles; block 420 of sintering the fluoridated apatite particles at a temperature of at least 950° C. to form a sintered body, and the block 430 of forming the scaffold from the sintered body. In some embodiments, one or more of the blocks 410-430 may be omitted, combined with other blocks, or performed in a different order than presented. For example, the blocks 420 and 430 may be performed substantially simultaneously, such as via sintering.

Block 410 of providing fluoridated apatite particles may include providing FA particles, FHA particles, or combinations of the foregoing. Providing fluoridated apatite particles may include providing a plurality of fluoridated apatite particles, such as FA, FHA, or combinations thereof. The plurality of fluoridated apatite particles may exhibit any of the average fluoridated apatite particle sizes disclosed herein. The fluoridated apatite particles may exhibit any of the bulk fluoridated apatite particle sizes disclosed herein (e.g., 60 μm to 200 μm).

In some embodiments, providing fluoridated apatite particles may include forming the fluoridated apatite particles, such as FA particles, FHA particles, or mixtures thereof. In some embodiments, a continuous aqueous precipitation method may be used to synthesize fluoridated apatite. The fluoridated apatite may be produced with a selected Ca/P ratio. For example, an FA with Ca/P ratio of 1.67 may be produced as set forth below. The FA may be synthesized under nitrogen atmosphere by mixing 250 ml of 1.2 M $Ca(NO_3)_2$ solution and 250 ml of 0.72 M $Na_2HPO_4$ solution containing stoichiometric ratios of NaF. Both $Ca(NO_3)_2$ and $Na_2HPO_4$/NaF solutions may be dispensed at a rate of 1.4 ml/min into a 12-liter reaction flask containing 10 liters of deionized water heated to a pre-selected isothermal temperature of 95° C. The reaction mixtures may be stirred at a selected speed during preparation. The stirring speed may be controlled, such as 50 rpm, to 300 rpm, 100 rpm to 200 rpm, or less than 500 rpm. The pH is maintained at 9.0, such as by auto-titrating with a pH-STAT controller and AUTO burette with a 1M NaOH solution. After which, the mixture may be digested for an additional 1 hour under the same isothermal conditions form FA. The FA may be obtained by filtering the mixture, and washing the mixture (e.g., four times) with doubly deionized water to remove all soluble byproducts (e.g., salts), and ethanol. The final residue may be dried, such as at 60° C. for 48 hours. While a specific example of forming FA is disclosed above, other techniques and reagents may be used for forming FA or FHA.

FA and FHA may be prepared by a precipitation method at an elevated temperature, such as at least 50° C. (e.g., 50° C. to 95° C.). FHA and FA may be synthesized by mixing 200 ml of 0.6M $Ca(NO_3)_2$ solution and 200 ml of 0.36 M $Na_2$ $HPO_4$ solution containing various concentrations of NaF at 1.4 ml/min into the 5-liter flask containing 4 liters of doubly deionized water pre-equilibrated to the target temperature. The stirring speed may be controlled such as at 200 rpm and the pH may be maintained such as at 9.0 by titration with 1M NaOH solution using a pH-STAT controller and AUTO burette. After mixing of the calcium and the phosphate/carbonate/fluoride solutions, the mixture may be digested for a selected duration, such as at least 1 hour, under the same conditions. The FA or FHA may be obtained by filtering the mixture, and may be washed one or more times (e.g., three times) with deionized water. The final residue may be oven dried, such as at 60° C. for 48 hours. The resulting unsintered solid may be ground into a fine powder and stored for later use for forming fluoridated apatite coatings. Various forms of FHA (25% to 75% of fluoride content) may be synthesized by changing the ratio of the reactants. X-ray diffraction and Fourier transform infrared spectroscopy may be used on the powders to analyze the crystallographic phase and the degree of fluorination, respectively.

The inventors have found the crystallinity and solubility properties of fluoridated apatite synthesized at 50° C. is closer to that of bone and dentin. The inventors have found the crystallinity and solubility properties of fluoridated apatite synthesized at 95° C. is closer to enamel (high crystallinity and lower solubility). Accordingly, the crystallinity and solubility of the fluoridated apatite may be selectively customized by controlling the temperature of the reaction mixture during formation of the fluoridated apatite.

The fluoridated apatite particles may be unsintered or sintered. For example, providing fluoridated apatite particles may include forming the fluoridated apatite particles into a cohesive mass such as a pellet, wafer, sheet, block, rod, plug, or any other body via pressing, rolling, molding, casting, or the like, prior to or contemporaneously with sintering the fluoridated apatite particles.

In some embodiments, providing fluoridated apatite particles may include forming the plurality of fluoridated apatite particles into a coherent body. The coherent body may consist of or consist essentially of FA, FHA, one or more dopants, or combinations of any of the foregoing. In some embodiments, additional materials may be present in the coherent body, such as a ceramic, metal, polymer, etc. Forming the plurality of fluoridated apatite particles into a coherent body may include pressing, rolling, molding, casting, adhering, or otherwise forming an at least partially bonded body or mass of fluoridated apatite particles.

The coherent body may be created by forming a slurry having fluoridated apatite particles and a sacrificial structural material. The slurry may be dried, cooled, or reacted to harden into the coherent body. The coherent body includes a solid or semi-solid structure containing fluoridated apatite particles and the sacrificial structural material (e.g., investment material). The coherent body may be frozen or compressed to form a green state part that remains intact as a solid unitary structure.

The sacrificial structural material may be selected to harden at a desired temperature or condition (800° C.-1500° C.), to provide a selected porosity, and/or to be removable from the coherent body (e.g., plurality of at least partially bonded fluoridated apatite particles) via one or more of combustion, melting, dissolution, vacuum, or any other technique for removing an investment material. For example, the sacrificial structural material may be a polymer, a salt, a ceramic, or the like, composed to dissolve or otherwise dissociate in selected conditions. The sacrificial structural material may be removed prior to, after, or concurrently with sintering the fluoridated apatite particles using any of the sintering techniques disclosed herein.

In some embodiments, the porous scaffoldings may be fabricated out of a fluoridated apatite slurry. The fluoridated apatite (e.g., FA) slurry may be used as an investment material or casting material. For example, scaffolds may be prepared using polymeric sponges as investment material or a mold, which are then infiltrated with the fluoridated apatite slurry containing monomers and initiators for rapid gelation via in situ polymerization. This gel sponge processing technique integrates gel-casting with polymer sponge methods. Next, the polymeric sponge can be removed (e.g., burned off at elevated temperatures (e.g., 1,050° C. to 1,250° C.)) and the remaining coherent body (e.g., fluoridated apatite scaffold) may be cleaned with distilled water.

In some embodiments, providing fluoridated apatite particles may include forming the fluoridated apatite particles into a predetermined shape. For example, fluoridated apatite scaffolding with pre-determined shapes (e.g., flat, tubular, or cubic) and porosities. Fluoridated apatite particles, DI water, and a binder (e.g., acrylamide/methylenebysacrylamide) may be mixed such as in a ball-mill and then, one or more of an initiator (e.g., Tetramethylenediamine), binder (e.g., carboxymethyl cellulose or Polyvinyl alcohol), dispersant, surfactant, or excess DI water may be added and mixed for duration (e.g., 12 hours). This slurry may be cured under vacuum, and sequentially poured over an infiltrated into a shaped polyether sponge as a frame for obtaining the desired shape, size, and porosity. The infiltrated sponge may be put under vacuum and a catalyst (e.g., ammonium persulfate) solution may be applied for facilitating polymerization. The sponges may be placed inside a nitrogen chamber to avoid surface contamination, which may prevent the polymerization process. After drying at room temperature, samples may be sintered to form the sintered body as disclosed in more detail below (e.g., at 1250° C. at a heating rate of 5° C./min).

Further methods of forming a coherent body of fluoridated apatite particles may include slip casting, freeze casting, sol-gel formation, foaming, or the like.

The scaffolds formed as disclosed herein induce bone formation within the scaffolding by utilizing dopants such as stem cell therapy and controlled delivery of osteogenic signals, which will significantly increase the strength of these materials.

The fluoridated apatite particles in the coherent body may be further subjected to sintering at a predetermined temperature. Block 420 of sintering the fluoridated apatite particles to form a sintered body may include sintering the fluoridated apatite particles prior to, contemporaneously with, or after providing the fluoridated apatite particles. The sintered body may have a denser bulk structure than the unsintered coherent body. The porosity of the sintered body may exhibit less porosity than the unsintered coherent body. Sintering the fluoridated apatite particles may include sintering the coherent body. Sintering the fluoridated apatite particles may include sintering a coherent body of fluoridated apatite particles that have been previously sintered. The sintered body may consist of or consist essentially of FA, FHA, one or more dopants, or combinations of any of the foregoing.

The fluoridated apatite particles may be sintered as one or both of a loose powder or in the cohesive body (e.g., polymer sponge impregnated with FA particles or pressed pellet of individual FA particles). Sintering the fluoridated apatite particles may include heating the fluoridated apatite particles to a temperature of at least about 950° C., such as about 950° C. to about 1,350° C., about 1,050° C. to about 1,250° C., about 1,050° C. to about 1,150° C., about 1,150° C. to about 1,250° C., at least 1,050° C., at least about 1,150° C., less than about 1,500° C., or less than about 1,250° C. The heating (e.g., sintering) may be carried out for at least 1 minute, such as about 1 minute to about 24 hours, about 1 hour to about 18 hours, about 2 hours to about 12 hours, about 4 hours to about 10 hours, about 20 minutes to about 4 hours, about 30 minutes to about 3 hours, about 1 hour to about 10 hours, about 8 hours to about 16 hours, at least about 2 hours, less than about 24 hours, or less than about 12 hours. The above-noted sintering times may be hold times at the sintering temperature. For example, a plurality of fluoridated apatite particles may be placed in a sintering oven that is ramped up to the sintering temperature at a selected rate (e.g., about 5° C./min, about 7° C./min., about 10° C./min., about 5° C./min. to 15° C./min, or about 1° C./min or more), maintains the sintering temperature for the selected duration, and ramps back down to ambient temperature at a selected rate (e.g., any of the rates disclosed above). The sintering temperatures within the ranges disclosed herein do not alter the chemical composition of the fluoridated apatites disclosed herein. Sintering may be carried out in an inert environment or an ambient environment.

Sintering the fluoridated apatite particles may include heating the fluoridated apatite particles in an inert atmosphere (e.g., $N_2$ or Argon), in a vacuum, in an open or oxidizing atmosphere (e.g., in the presence of oxygen, carbon dioxide, $N_2$, etc.), or combinations of any of the foregoing.

Sintering the fluoridated apatite particles to form a sintered body may include sintering the fluoridated apatite particles (e.g., coherent body) at a temperature sufficient to burn out any investment or mold material such as a polymer, so that substantially only the fluoridated apatite or other selected materials desired for implantation remain. In such embodiments, the as-cast fluoridated apatite particles (e.g., coherent body) and the material the fluoridated apatite particles were cast in (e.g., polymer sponge or matrix material) may be subjected to sintering.

The sintered fluoridated apatite particles may exhibit the surface morphology, porosity, zeta potential, average particle size, or any other characteristics of any of the sintered fluoridated apatite particles disclosed herein. For example, the sintered body may include sintered fluoridated apatite particles having a spherical, semi-spherical, prismatic, pseudo-prismatic, ellipsoid, or irregularly rounded shape and are devoid of rod-like or needle-like fluoridated apatite particles.

As noted above, the sintered fluoridated apatite particles are densified via the sintering process while the polymer material is combusted or melts out of the coherent body. The shrinkage of the fluoridated apatite particles during sintering is reproducible (about 15% upon sintering). Accordingly, the techniques disclosed herein provide the ability to custom make scaffoldings for the desired shapes and sizes to fit the clinical needs of grafts for reconstructive surgeries in plastic, orthopedic and dental surgeries. Unfortunately, tensile properties of pure apatite ceramics are limited. For example, unsintered apatite ceramics exhibit a hardness value about of 5.1 GPa and fracture toughness value of about 2.0 $MPa \cdot m^{1/2}$. When compared to the fracture toughness of human bone (about 12 $MPa \cdot m^{1/2}$), apatite's toughness is relatively poor. Thus, the fluoridated apatite scaffolds disclosed herein may be used as heavy-loaded implants after sintering to improve strength.

Figure 5A:
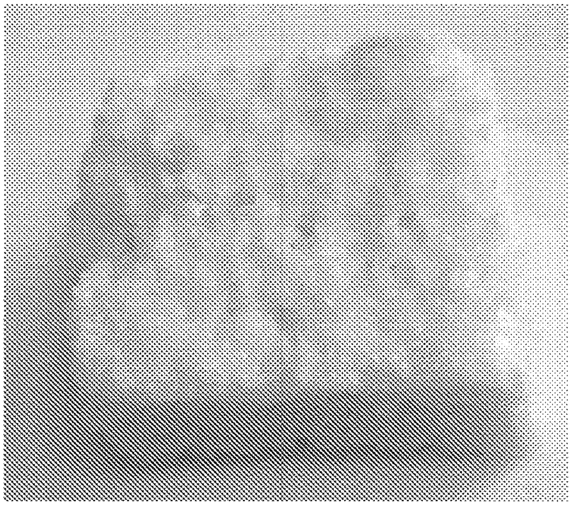
FIGS. 5A and 5B are a photo and a scanning electron photomicrograph (at 50× magnification) of porous apatite, respectively.
Figure 5B:
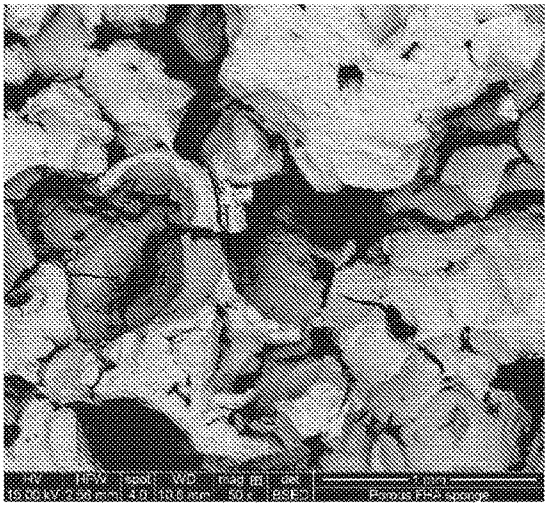

The scaffolds disclosed herein (e.g., FA scaffolds) may exhibit at least 10% porosity, such as 30% to 70% porosity. Accordingly, the scaffolds may provide a ready delivery means for one or more dopants. Such scaffolds may be used as bone fillers, such as for dental applications or the like. FIGS. 5A and 5B are a photo and a scanning electron photomicrograph (at 50× magnification) of porous apatite, respectively. FIGS. 5A and 5B show bulk and microporosity of the scaffolds disclosed herein. The bulk porosity is defined by the shape of the investment material used to form the scaffold. The microporosity is formed by the agglomeration of the fluoridated apatite particles in the scaffold.

Returning to FIG. 4, the block 430 of forming the scaffold from the sintered body may include shaping or sizing the sintered body into a selected shape and size. For example, the sintered body may be shaped and sized to fit a pocket in tissue of a subject. Forming the scaffold from the sintered body may include machining, grinding, lasing, carving, polishing, lapping, or otherwise removing material from the sintered body. The scaffold may be sized and shaped as a percutaneous implant, an osseointegrated implant, a dental implant, a bone implant, bone replacement, or the like.

In some embodiments, forming the scaffold may be carried out substantially simultaneously with sintering the coherent body to form a sintered body. For example, the forming the scaffold and sintering the coherent body may both be carried out via sintering. In such embodiments, the coherent body may be provided in a size and shape such that the sintered body may be the scaffold (e.g., implantable size and shape). Providing such a shape may be provided or formed by one or more of molding, grinding, cutting, lapping, etc.

The method 400 may include doping the fluoridated apatite particles, coherent body, sintered body, or scaffold with one or more dopants, such as any of the dopants disclosed herein. Doping the fluoridated apatite particles, coherent body, sintered body, or scaffold with one or more dopants may include doping the fluoridated apatite particles, coherent body, or sintered scaffold with any of the dopants disclosed herein. For example, adipose tissue (e.g., ASCs) is an accessible source of stem cells and they have the ability to differentiate into a tri-lineage pathway: bone, cartilage, and/or adipose tissue. When appropriately stimulated with osteogenic signals, ASCs will differentiate into an osteoblast phenotype. One such transduction signal is from bone morphogenetic protein-2 (BMP-2). Accordingly, the one or more dopants may include one or more of autograft materials, allograft materials, or synthetic materials.

Doping the fluoridated apatite particles may include mixing one or more dopants into the fluoridated apatite particles prior to, contemporaneously with, or after providing the fluoridated apatite particles or forming the coherent body of fluoridated apatite particles. For example, doping the fluoridated apatite particles may include adding one or more dopants to the plurality of fluoridated apatite particles prior to forming the coherent body, or coating at least a portion of the coherent body with one or more dopants after forming the coherent body. Each of the one or more dopants may be present in amounts composed to stimulate bone growth, cell differentiation, or soft tissue growth, such as at least 1 nanogram (ng), 10 micrograms (μg) to 10 milligrams (mg), about 25 μm to 1 mg, 50 μg to 500 μg, or less than 1 mg.

Combinations of dopants may be utilized to provide controlled release of one or more dopants in vivo. For example, ASCs may be used with BMP-2 and a hydrogel such as keratose, where keratose is relatively stable in vivo to allow for controlled release of dopants disposed therein. For example, the keratose may be applied as a coating over the scaffold, where upon degradation of the keratose the dopants there beneath are released. For example, the keratose may dissolve to release growth factors such as BMP-2. In some examples, the dopants may be present in a layered systems where multiple layers of dopants are each disposed beneath a layer of hydrogel such as keratose. Accordingly, time released benefits may be realized using the scaffolds disclosed herein.

Doping the coherent body, sintered body, or scaffold may include applying a solution containing the one or more dopants into or onto the coherent body, sintered body, or scaffold. For example, one or more of the dopants may be suspended, dispersed, or dissolved in a liquid medium which is applied to the coherent body, sintered body, or scaffold, such as via immersing, spraying, pipetting, aliquoting, or any other liquid application technique. In embodiments, BMP-2 may be dispersed in a keratose hydrogel, which may be poured over a scaffold and allowed to incubate. Similarly, a scaffold may be wetted and loaded with a suspension of ASCs.

In some examples, doping the scaffold may include disposing the scaffold in the tissue of an implantee, such as soft tissue to deposit autologous tissues, growth factors, etc. in the scaffold prior to final implantation in a bone.

Experiments were carried out to determine the effectiveness of various embodiments of fluoridated apatite materials for adhering to soft tissue cells. To determine the extent of cell adhesion on cells that are relevant to percutaneous applications, keratinocytes were grown directly on the surface of the manufactured apatite (HA, FHA, and FA) pellets. For this assessment, HaCaT cells (T0020001; AddexBio Technologies, San Diego, CA) were grown in the recommended growth media until confluent.

A cell density of $1\times10^5$ cells/cm$^2$ surface area was suspended in 75 μL of culture media and carefully placed as a droplet on each pellet in individual wells of a 12-well plate. Additionally, titanium pellets (RD-128Ti; BioSurface Technologies Corporation, Bozeman, MT) were obtained and used as experimental controls. Before being utilized in cell or bacterial experiments, Titanium pellets were passivated, washed in 70% ethanol, and steam autoclaved. As the titanium pellets were larger than the HA, FHA, and FA pellets, the cells were suspended in 150 μL of culture media to ensure the topmost face of the pellet was thoroughly seeded with cells. The samples were moved to a humidified incubator for a period of two hours to permit initial cell adhesion. Following this two-hour period, each well was slowly filled with 2 mL of fresh media, fully submerging the samples.

To count the number of adherent cells following the two-day experiment, pellets were gently washed in phosphate buffered saline (PBS), moved to a new culture plate, and incubated with 0.5 mL of 0.25% Trypsin. To inactivate the Trypsin, 0.5 mL of fresh media containing fetal bovine serum (FBS) was added to each pellet. The Trypsin/media solution was then flushed across the face of the pellet several times with a pipette in order to remove any remaining adherent cells. A hemocytometer was used to count the cells that had adhered to the surface. Data is reported as the percentage of cells counted following the two-day period relative to the initial quantity of cells seeded on each respective pellet.

Figure 6:
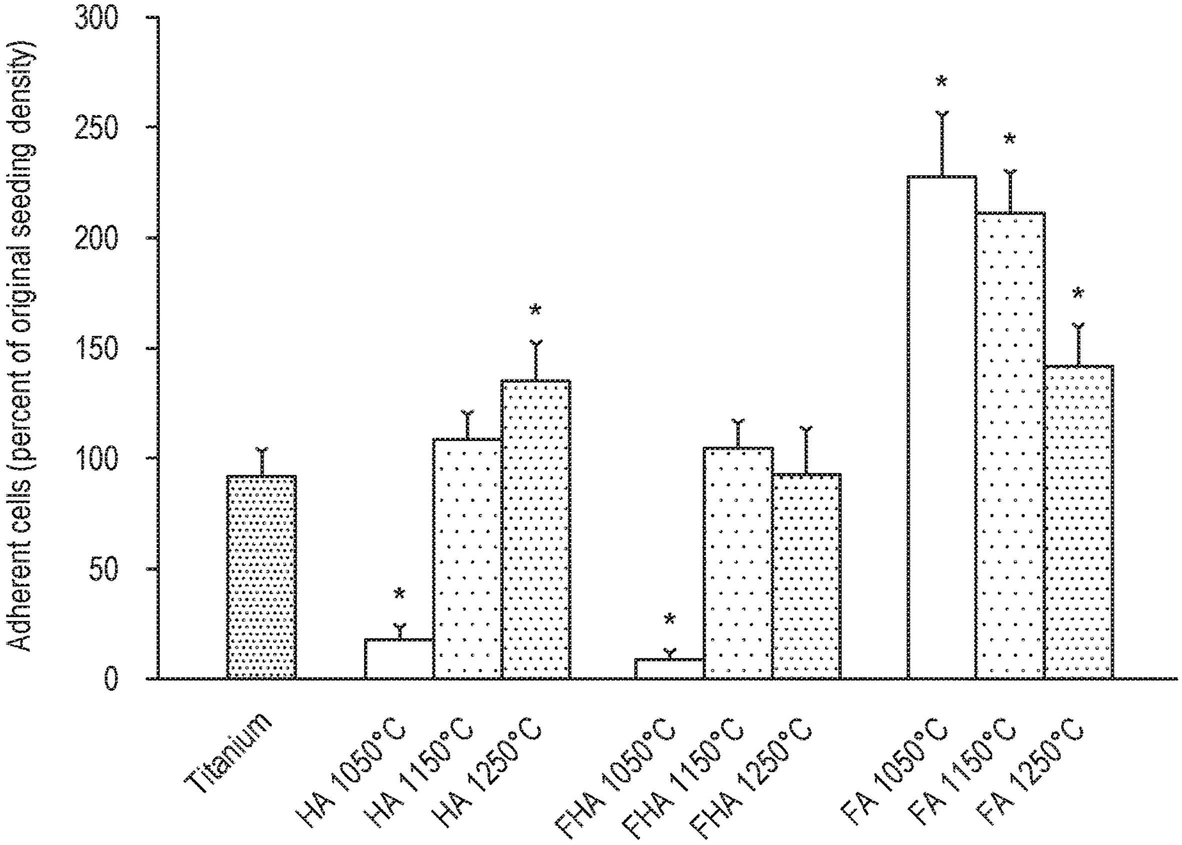
FIG. 6 is a bar chart showing the enumerated adherent HaCaT cells, from each sample surface two days after seeding.

FIG. 6 is a bar chart showing the enumerated adherent HaCaT cells, from each sample surface two days after seeding. Results are presented as means±SEM. Expressed as a percentage of adherent cells relative to the original seeding density, titanium pellets had a normalized adherence rate of 92±12%. HA pellets sintered at 1050° C. had a significantly lower cell count than the titanium pellets. Conversely, HA pellets sintered at 1250° C. had significantly more adherent cells after two days compared to titanium pellets. Similar to HA pellets sintered at 1050° C., FHA pellets sintered at this temperature had a very low adherence rate. FHA pellets sintered at 1150° C. and 1250° C. had adherence rates comparable to those observed on HA pellets sintered at the same temperatures.

The largest difference in the two-day adhesion and proliferation rate of HaCaT cells was observed within the groups of FA pellets sintered at 1050° C. and 1150° C. (FIG. 5). FA pellets sintered at 1050° C. had an adherence rate of 227±28%, while FA pellets sintered at 1150° C. had an adherence rate of 210±18%. There were no statistically significant differences between these two groups; however, the adherence rate observed on these two surfaces was significantly higher than any other experimental group. FA pellets sintered at 1250° C. had a slightly lower adherence rate (143±17%) than the FA pellets sintered at the lower temperatures (1050° C. or 1150° C.). Nonetheless, this group maintained a significantly higher HaCaT cell adherence over the control titanium pellets.

Keratinocytes adherence to FHA and/or FA surfaces may drive the differentiation of epithelial cells into mature, terminally differentiating phenotypes such as those of suprabasal epithelial cells, a transition highly important for preserving the integrity of the epithelial tissue attachment at the percutaneous implant interface. The extent of cell differentiation of various apatite materials formed at various sintering temperatures was experimentally determined.

Figure 7:
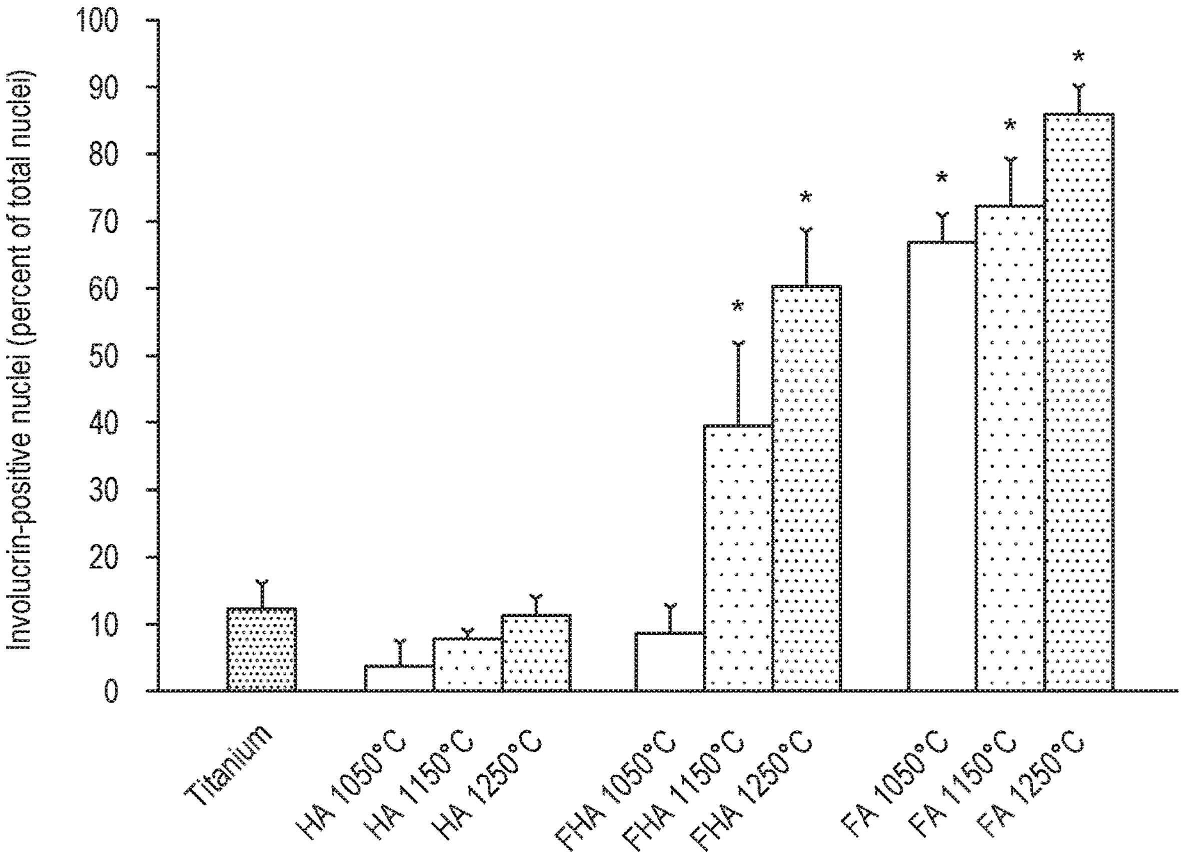
FIG. 7 is a bar chart showing the enumerated Involucrin-positive nuclei on the respective samples.

Involucrin, a marker of terminal differentiation in keratinocytes, was utilized in immunocytochemistry experiments to provide a semi-quantitative analysis of the rate of differentiation of HaCaT cells. Results from these experiments further suggested the enhanced ability of FA surfaces to promote terminal differentiation of keratinocytes. FIG. 7 is a bar chart showing the enumerated Involucrin-positive nuclei on the respective samples. Expressed as a percentage of Involucrin-positive cells relative to the total number of nuclei, keratinocyte cells cultured on FA pellets for two days were undergoing differentiation to a high degree. FA pellets sintered at 1250° C. had the highest relative levels of differentiation (86±4%), followed by FA sintered at 1150° C. (72±7%), and finally, FA sintered at 1050° C. (67±4%). This is significantly higher than either the titanium controls or any of the HA pellets, all of which had an average of approximately 10% differentiated cells. Similar to FA, FHA pellets sintered at high temperatures also induced significantly more keratinocyte differentiation than HA or titanium. Although the relative number of differentiated cells on FHA sintered at 1050° C. (8±4%) was similar to that of titanium and HA, there were significantly more Involucrin-positive cells observed on FHA pellets sintered at both 1150° C. (40±12%) and 1250° C. (60±8%).

Similar to the cell adhesion experiments described above, bacteria (*S. aureus*) were grown on the top face of the various pellets (HA, FHA, and FA at the sintering temps used in the above-described experiments) and the rate of adherence was observed after a predetermined period of time. The resultant colony forming units (CPUs) were normalized to the surface area available for bacterial adhesion. Although the mean adhesion and proliferation rates varied considerably amongst the experimental groups, no significant differences were observed within or between these groups. Thus, the experiment did not reveal any statistically significant differences between any of the fluoridated surfaces and titanium for hosting bacteria. Accordingly, the inventors believe tissue cells can be preferentially bonded to the fluoridated apatites disclosed herein without increasing bacterial adhesion.

As demonstrated herein, fluoridated apatite surfaces (especially FA surfaces) sintered at 1050° C. to 1,250° C. (and more particularly 1050° C. to 1150° C.), are more conducive to keratinocyte adhesion and differentiation when compared to titanium surfaces and HA surfaces.

Figure 8:
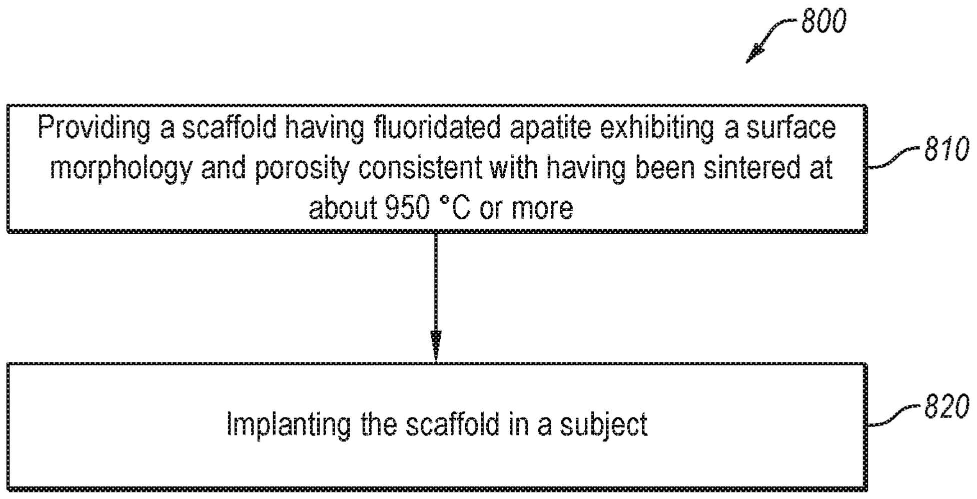
FIG. 8 is a flow chart of a method of using a scaffold having fluoridated apatite, according to an embodiment.

FIG. 8 is a flow chart of a method 800 of using a scaffold having fluoridated apatite, according to an embodiment. The method 800 includes the block 810 of providing a scaffold having fluoridated apatite exhibiting a surface morphology and porosity consistent with having been sintered at about 950° C. or more and the block 820 of implanting the scaffold in a subject.

The block 810 of providing a scaffold having fluoridated apatite exhibiting a surface morphology and porosity consistent with having been sintered at about 950° C. or more may include providing any of the scaffolds disclosed herein. Providing a scaffold having fluoridated apatite exhibiting a surface morphology and porosity consistent with having been sintered at about 950° C. or more may include providing a scaffold having fluoridated apatite particles sintered at any of the temperatures disclosed herein (about 950° C. to about 1350° C. or about 1050° C. to about 1250° C.), having any of the zeta values disclosed herein, having any of the surface morphologies disclosed herein, or any of the properties of sintered fluoridated apatite particles disclosed herein. The scaffold may consist of or consist essentially of FA, FHA, one or more dopants, or combinations of any of the foregoing. The scaffold may carry any of the dopants disclosed herein, such as one or more of a differentiation promoter, stem cells, or demineralized bone matrix. The scaffold may be sized and shaped for an at least partial bone replacement, an osseointegrated implant, a dental implant, or the like. Providing a scaffold include making the scaffold, such as by using any of the techniques for making scaffolds disclosed herein. Making the scaffold may include adding one or more dopants to the scaffold as disclosed herein.

The surface morphology of the sintered fluoridated apatite particles of the scaffold may include spherical, semi-spherical, prismatic, pseudo-prismatic, ellipsoid, or irregularly rounded fluoridated apatite particles that are devoid of rod-like or needle-like fluoridated apatite particles.

The scaffold may be sized and shaped as disclosed herein, such as sized and shaped to be used as a bone implant, an osseointegrated implant, or a dental implant.

Providing the scaffold may include forming the scaffold as disclosed herein.

The block 820 of implanting the scaffold in a subject may include implanting the scaffold into the tissue of a subject, such as into the skin, bone, or other tissues of a subject. For example, implanting the scaffold in a subject may include positioning the implant within a pocket in a bone of a subject, such as in a jaw, hip, vertebrae, femur, etc. For example, an osseointegrated scaffold may be inserted into bone whereby the fluoridated apatite contacts one or both of the bone or soft tissue of the subject. Implanting the scaffold in a subject may include surgically implanting the scaffold into the tissue of a subject. Implanting the scaffold in a subject may include closing the implantation site, such as by suturing.

Implanting the scaffold may include one or more of sizing or shaping the scaffold as disclosed herein.

The method 800 may include preparing an implantation site such as by removing tissue (e.g., bone) from an implantation site in a patient. For example, preparing an implantation size may include removing at least some bone to form a pocket in a bone. In such embodiments, the scaffold may be shaped and sized to fit in the pocket.

Preparing the implantation site may include cleaning the implantation site, such as cleaning the interface between the bone of the subject and the scaffold. Such cleaning may include washing with water or another fluid (e.g., iodine, soap, alcohol, etc.).

The method 800 may include implanting the scaffold in soft tissue prior to implanting the scaffold in bone, such as to allow the one or more dopants to produce autograft cells. The scaffold may be disposed in the soft tissue for at least a week, such as 1 week to 3 months.

The method 800 may include adding one or more dopants to the scaffold, such as any of the dopants disclosed herein.

Working Examples

HA was provided. FHA and FA were synthesized by mixing 250 ml of 1.2 M $Ca(NO_3)_2$ solution and 250 ml of 0.72 M $Na_2HPO_4$ solution containing various stoichiometric ratios of NaF. Both $Ca(NO_3)$ and $Na_2HPO_4$/NaF solutions were dispensed at a rate of 2.4 ml/min into a 12-liter reaction flask containing 10 liters of deionized water that was heated to a pre-selected isothermal temperature of 95° C.

Pellets were prepared from the raw HA, FHA, FA powders. Briefly, 65 μL sterile water was added to 300 mg of HA, FHA, FA powders, respectively, and mixed thoroughly using a mortar and pestle. The mixture was transferred to a 10 mm diameter die and compacted under vacuum using a manual hydraulic press (GS15011; Specac, Reflex Analytical Corp, Ridgewood, NJ). Sample pellets were then sintered at 1050° C., 1150° C., and 1250° C. using a box furnace (ST-1600C-888; Sentro Tech Corp, Strongsville, OH). The sintering cycle was comprised of a two-hour isothermal hold at the desired temperature with a heating/cooling rate of 7° C./min. After sintering, pellets were cleaned with 70% ethanol, air-dried, and steam sterilized. The samples included sterile titanium pellets; HA pellets sintered at 1050° C., 1150° C., and 1250° C.; FHA pellets sintered at 1050° C., 1150° C., and 1250° C.; and FA pellets sintered at 1050° C., 1150° C., and 1250° C.

The sample pellets above were utilized for cellular adhesion and gene expression experiments.

Cellular Adhesion

Osteoblast cells and bone marrow derived stromal cells (BMSCs), were grown directly on the surface of the sample pellets. For this assessment, osteoblast cells (CRL-11372; ATCC, Manassas, VA) were grown in the recommended growth media until confluent. BMSC cells were harvested from rat incisors (CD Hairless—strain 184; female age 3-4 mos; Charles River, Wilmington, MA) and cultured in MEM alpha media (32571036; Gibco-ThermoFisher, Waltham, MA) supplemented with fetal bovine serum (FBS; 10%), pen-strep (1%), and ascorbic acid (1%).

For each separate cell type, a cell density of $1\times10^5$ osteoblast or BMSC cells/cm$^2$ surface area, respectively, was suspended in 75 μL of culture media and carefully placed as a droplet on each sample pellet in individual wells of a 12-well plate. Sterile titanium pellets (RD-128Ti; BioSurface Technologies Corporation, Bozeman, MT) were obtained and used as experimental controls. As the titanium pellets were larger than the HA, FHA, and FA pellets, the cells were suspended in 150 μL of culture media to ensure the topmost face of the pellet was thoroughly seeded with cells. After seeding the cells, the samples were moved to a humidified incubator for a period of two hours to permit initial cell adhesion on the samples. Following this two-hour period, each well was slowly filled with 2 mL of fresh media to fully submerge the samples. To count the number of adherent cells following the two-day experiment, pellets were gently washed in phosphate buffered saline (PBS), moved to a new culture plate, and incubated with 0.5 mL of 0.25% Trypsin. To inactivate the Trypsin, 0.5 mL of fresh media (containing FBS) was added to each pellet. The Trypsin/media solution was then flushed across the face of the pellet several times with a pipette in order to remove any remaining adherent cells. A hemocytometer was used to count the cells that had adhered to the surface. Data was calculated as the percentage of cells counted following the two-day period relative to the initial quantity of cells seeded on each respective pellet.

Figure 9:
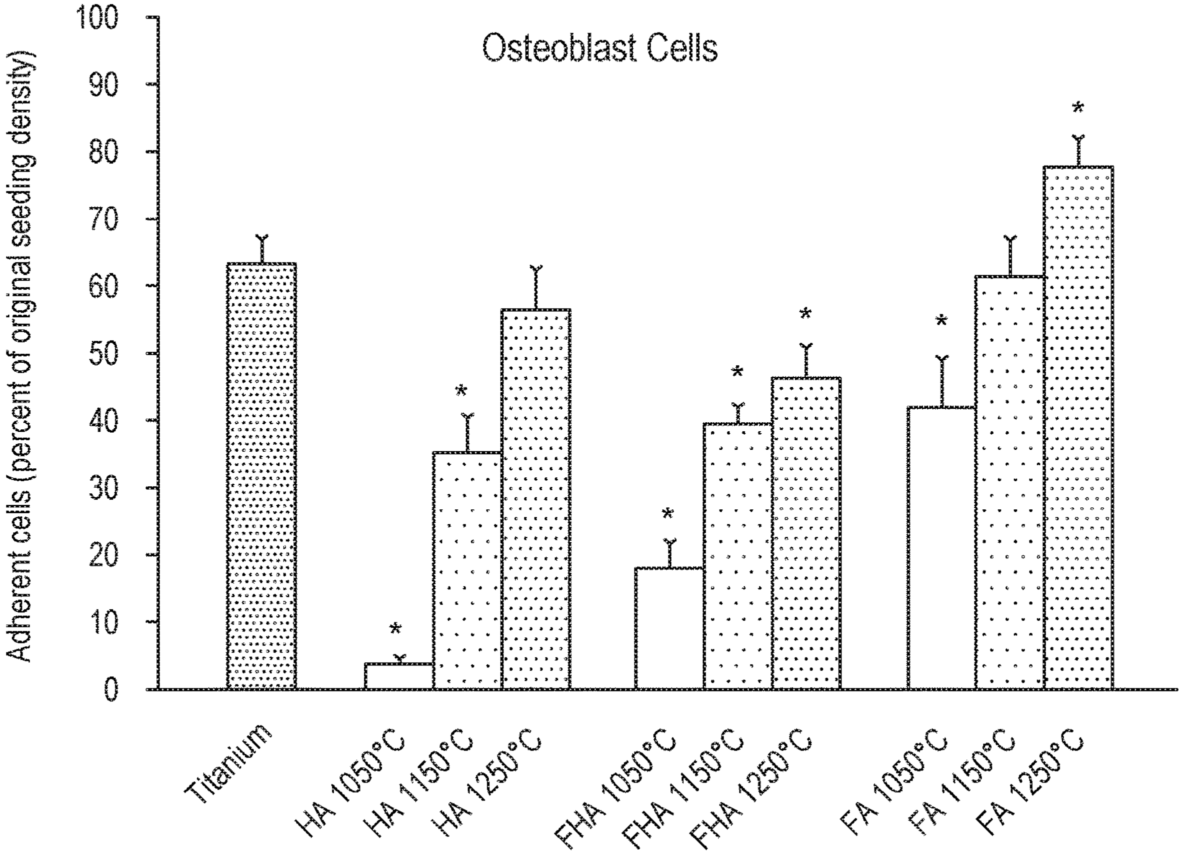
FIG. 9 is a bar chart of adhesion properties of osteoblasts to various samples.

FIG. 9 is a bar chart of adhesion properties of various samples to osteoblasts. The percentage of osteoblast cells that were adhered to the titanium control pellets following the two-day experiment was 88.02±7.25%. HA pellets sintered at 1050° C. and 1150° C. had significantly ($p<0.05$) fewer adherent cells than titanium. There was no statistical difference between HA sintered at 1250° C. and titanium samples.

The adhesion percentage of the FHA pellets was similar to what was observed on the HA pellets, with increasing cell adhesion in response to increased sintering temperatures. All sintering temperatures of HA and FHA produced an adhesion response less than that of titanium.

The only increase in osteoblast adhesion and proliferation was observed in the FA group. FA sintered at 1250° C. had a significantly higher adhesion rate than titanium, with an observed value of 108.59±6.21%. No increase in adhesion was observed in the FA pellets sintered at 1050° C. and 1150° C., and FA sintered at 1050° C. surprisingly had a reduced adhesion rate compared to titanium.

Figure 10:
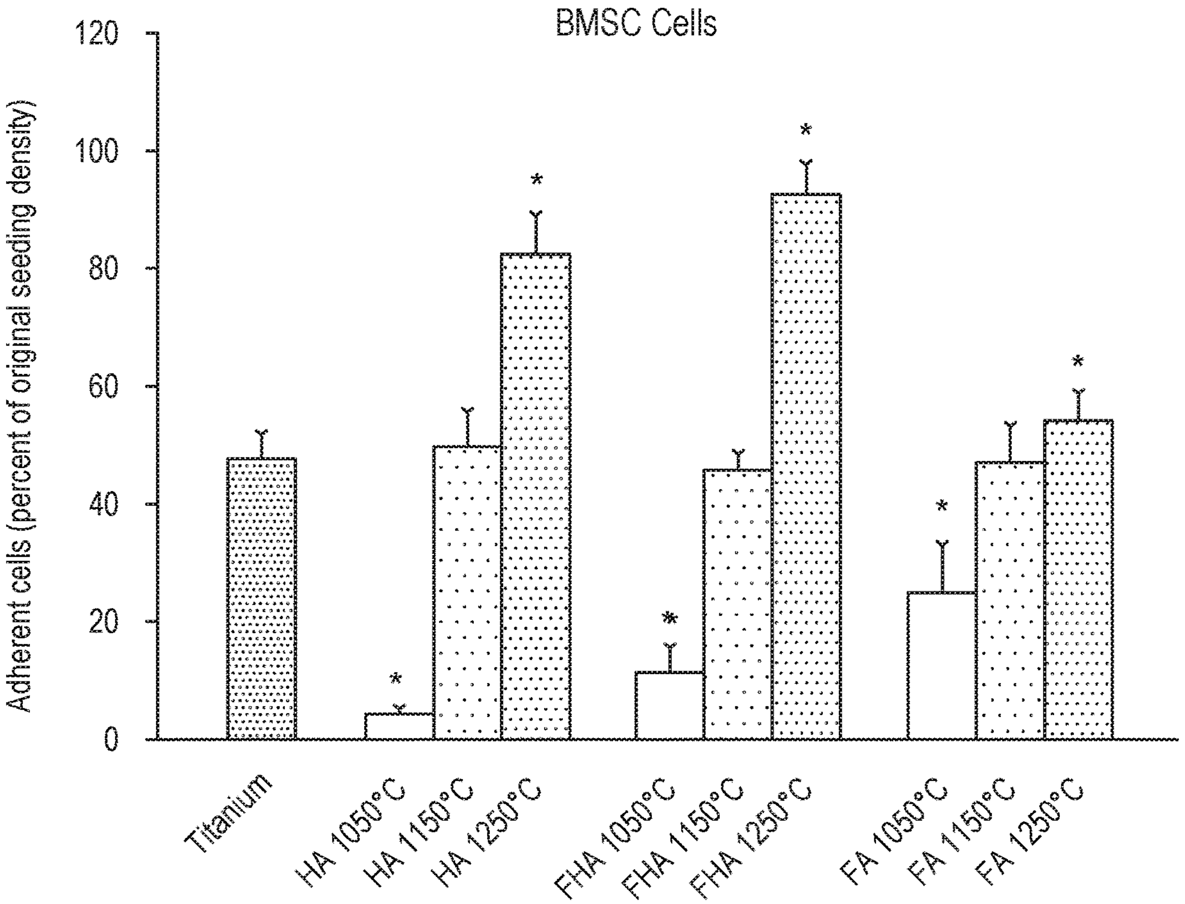
FIG. 10 is a bar chart of adhesion properties of BMSCs to various samples.

FIG. 10 is a bar chart of adhesion properties of various samples of BMSCs. In the two-day culture experiments utilizing the BMSC cells, sintering the HA, FHA, and FA pellets at 1250° C. increased the rate of adhesion and proliferation the greatest. Compared to titanium surfaces (47.84±3.33%), the percent of cells that had adhered and proliferated was significantly increased on the HA (83.47±7.25%), FHA (93.80±5.94%), and FA (54.96±5.53%) pellets sintered at 1250° C. Cell adhesion and proliferation on each of HA, FHA, and FA sintered at 1050° C. was significantly reduced compared to titanium. Such a decreases in cell adhesion shows a sintering-dependent effect on BMSC activity.

Gene Expression

The gene expression of various markers associated with bone remodeling was examined Surface induced differentiation of the osteoblasts was quantified using standard qRT-PCR techniques to examine mRNA expressions for osteocalcin (OCN) and secreted phosphoprotein 1 (SPP1) on the various sample pellets.

Sample pellets of titanium, HA, FHA, and FA (sintered at various temperatures as disclosed above) were placed in separate wells of a culture plate. The samples were seeded with cells. Some wells of a culture plate were left without a sample pellet, but were seeded with cells to examine normal gene expression patterns of the cells not exposed to the sample materials. Following the conclusion of the cell culture experiments, cells were removed from the pellets and total RNA was extracted utilizing an RNeasy Mini Kit (74104; Qiagen, Germantown, MD), according to the manufacturer's instructions. RNA concentration and purity was then examined using a NanoDrop spectrophotometer (ThermoFisher). Gene analysis was then performed using the QuantStudio™ 3 Real-Time PCR System (ThermoFisher), with each reaction run in triplicate. All values were normalized to the housekeeping gene Glyceraldehyde-3-phosphate dehydrogenase (GAPDH), and are expressed as ΔΔct. The following primer sequences were utilized:

```
GAPDH:
Forward-(5') ACCACCATGGAGAAGGC (3')

Reverse-(5') GGCATGGACTGTGGTCATGA (3')

Osteocalcin:
Forward-(5') AAGCCCAGCGACTCTGAGTCT (3')

Reverse-(5') AGGTAGCGCCGGAGTCTATTC (3')

SPP1:
Forward-(5') TGGCCGAGGTGATAGTGTGGTTA (3')

Reverse-(5') AACGGGGATGGCCTTGTATGC (3')
```

Figure 11:
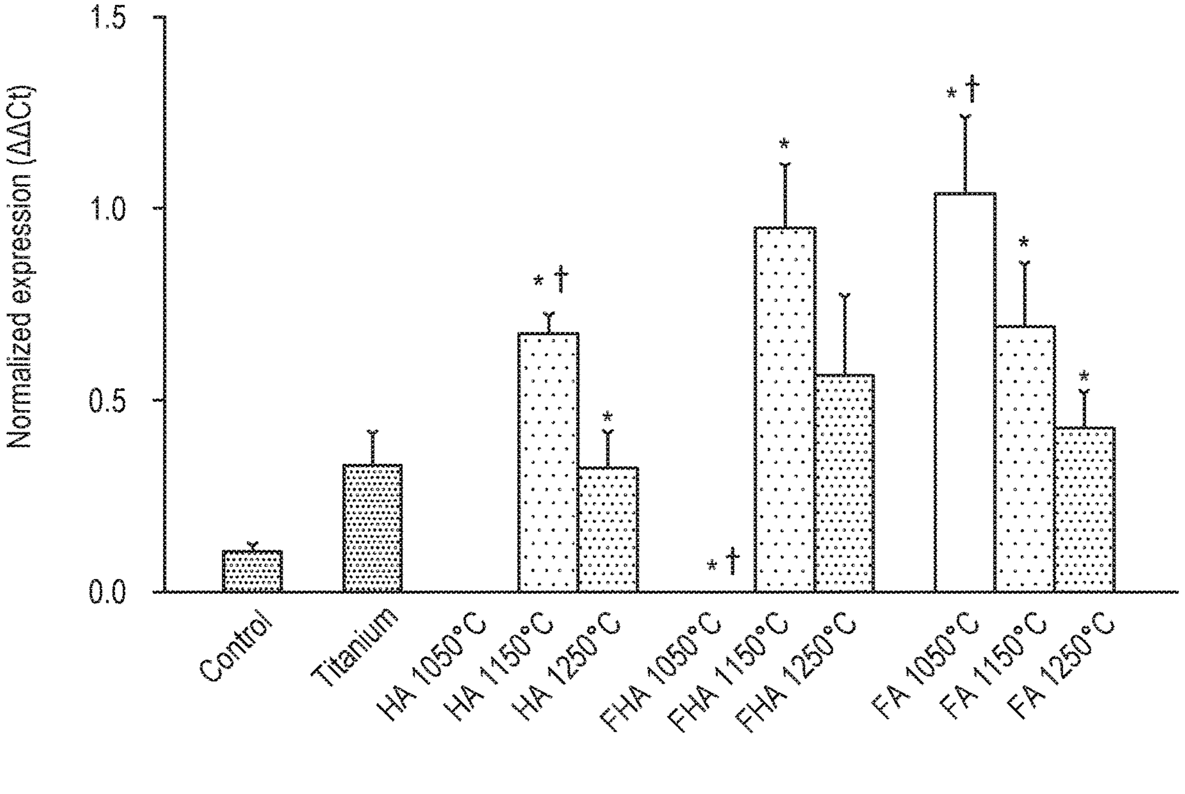
FIG. 11 is a bar graph of gene expression of osteocalcin on various samples.

FIG. 11 is a bar graph of gene expression of osteocalcin on various samples. Compared to both the control and titanium samples, a significant increase in expression was observed on the HA 1150° C., FHA 1150° C., and FA 1050° C. samples. The FHA 1250° C., FA 1150° C., and FA 1250° C. groups had increased osteocalcin expression compared to the control cell group and the titanium cell group. Although only small differences were observed compared to titanium, the HA 1250° C. group had greatly increased osteocalcin expression compared to the control cell group.

Figure 12:
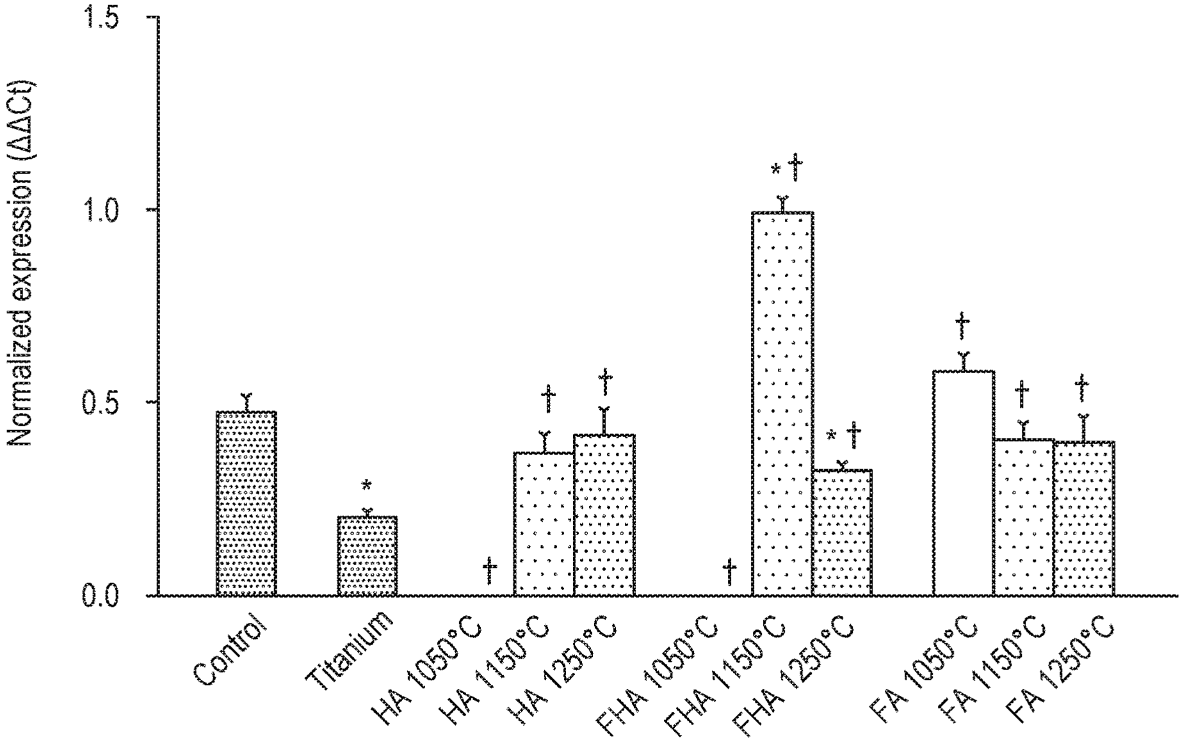
FIG. 12 is a bar graph of gene expression for SPP1 on various samples.

FIG. 12 is a bar graph of gene expression for SPP1 on various samples. Compared to the cells that were seeded in the empty wells (control), expression of this gene on the titanium surfaces was significantly reduced. Excepting HA 1050° C. and FHA 1050° C., which did not have any cells as described previously, all other samples had an increased SPP1 expression compared to titanium. The FA 1050° C. group had a slightly increased expression compared to the control group. The only group to have a significantly increased SPP1 expression compared to both the titanium and control groups was FHA sintered at 1150° C., which had roughly twice the expression of the control cells.

Time Lapse Cell Adhesion

In a time lapse experiment, adipose derived mesenchymal stromal cells (ADSC) were seeded on sample pellet surfaces and examined 2 and 10 days post-seeding. The sample pellets included titanium, HA sintered at 1150° C. and 1250° C., FHA sintered at 1150° C. and 1250° C., and FA sintered at 1150° C. and 1250° C. The pellets were disk shaped. The samples include a cell drop (control) sample.

The ADSC cells were obtained from Cyagen (Santa Clara, CA; RASMD-01001), maintained in ADSC growth media (Cyagen, Santa Clara, CA; GlUXMD-900011) supplemented with 10% heat-inactivated fetal bovine serum (Gibco, Grand Island, N.Y.), and incubated at 37° C. in a 5% $CO_2$ incubator.

ADSC were plated on a cell culture plate (cell drop control), titanium pellet, HA pellets sintered at 1150° C. and 1250° C., FA pellets sintered at 1150° C. and 1250° C., and FHA pellets sintered at 1150° C. and 1250° C. The ADSC's were plated at a density of 13,600 cells/$cm^2$ for the analysis of cell viability at day 2 post seeding and at 1,300 cells/$cm^2$ for analysis at day 10 post seeding. Following incubation for the pre-set time points cell viability was evaluated using an alamarBlue® assay (Invitrogen, Carlsbad, CA). ADSC were exposed to a 10% alamarBlue® solution for 2 hours at 37° C., and then fluorescence read (FLx800, BioTek, Winooski, VT) following the manufacturers instructions. All data is reported as viability relative to cell drop control.

Figure 13:
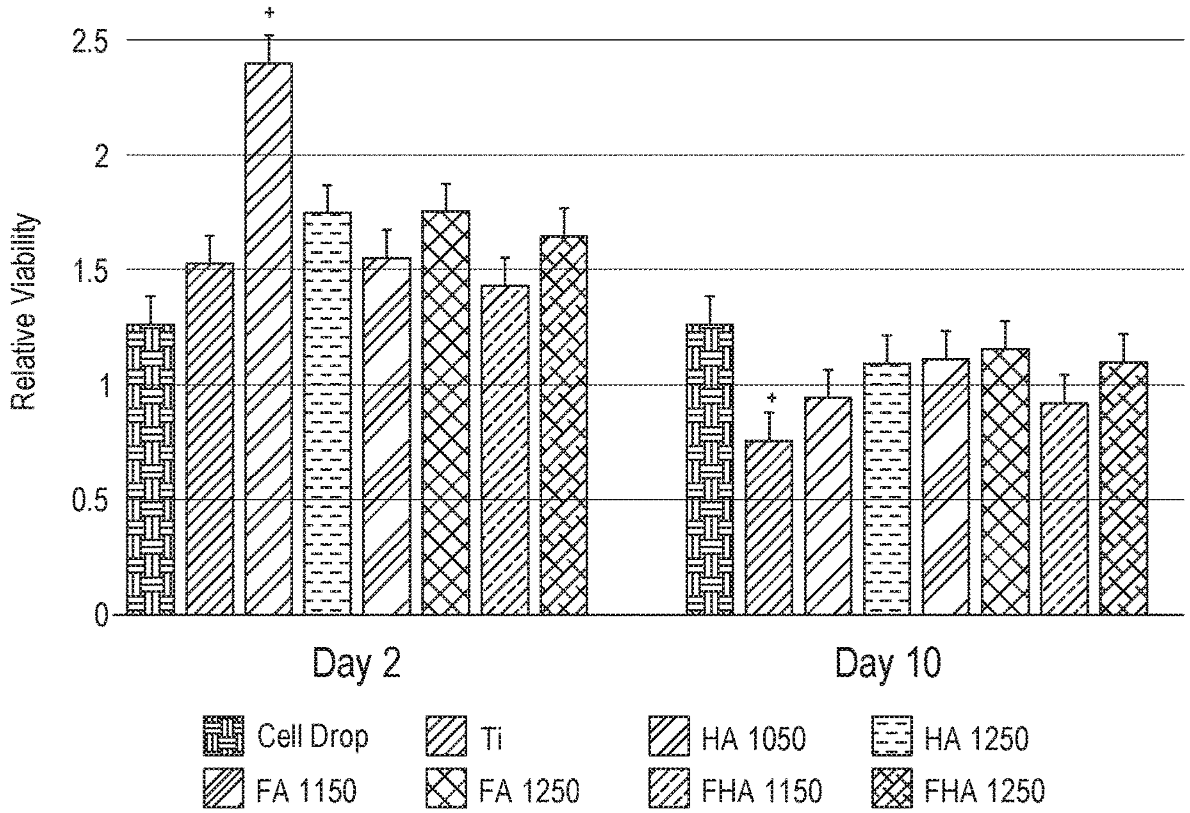
FIG. 13 is a bar graph of the relative cell viability of various samples.

FIG. 13 is a bar graph of the relative cell viability of various samples. Two days post seeding there were more viable cells on the HA 1150° C. pellet (1.9±0.09) compared to the other samples. By 10 days post seeding, the Ti sample (0.6±0.07) had fewer viable cells than the cell drop control ($p<0.01$). There were little to no statistical differences between the cell drop control and the apatite disks or between the Ti disk and apatite disks ($p>0.05$) at 10 days.

Time Lapse Gene Expression

ADSC were plated on the samples (titanium, HA sintered at 1150° C. and 1250° C., FHA sintered at 1150° C. and 1250° C., and FA sintered at 1150° C. and 1250° C.) at the same densities and duration as described in the time lapse cell viability examples. Cells were removed from the surfaces with trypsin (% solution) and total RNA extracted (RNeasy Mini Kit, Qiagen). RNA quality and quantity were evaluated (2200 TapeStation, Agilent) and then reversed transcribed (TaqMan Gene Expression Master Mix, ThermoFisher). Gene expression was then quantified using real-time PCR (QuantStudio 12K Flex; ThermoFisher) with gene-specific primers for osteopontin (SPP1; RN00681031_m1, Thermo Fisher ID; NM_012881.2, NCBI Reference Sequence), runt-related transcription factor 2 (Runx2; RN01512298_m1; NM_001278483.1), and alkaline phosphatase (ALK Phos; RN-1516028_m1; NM_013059.1). Samples were run in triplicate. All values were normalized to the housekeeping gene 18s ribosomal RNA (Hs999999901_s1; X03205.1, GenBank) and data reported as ΔΔct.

ADSC cells seeded on the different surfaces for 2 or 10 days were fixed in 10% formalin, and then incubated with primary antibody for ALK (1:400, ab108377; Abcam) osteocalcin (1:400, ab13420; Abcam), and osteopontin (1:400, ab8448; Abcam). The samples were then incubated with fluorescently labeled secondary antibodies for osteocalcin (ab175472; Abcam), osteopontin (A31573; Invitrogen), and ALK (A31573; Invitrogen). Samples were imaged on a Nikon A1R confocal microscope at 20× magnification.

Experiments were performed in quadruplicate, with data reported as mean±SEM. Group differences in ADSC viability and gene expression were evaluated by ANOVA followed by a Tukey's post hoc test (JMP, SAS Institute). Significance was set at $p<0.05$.

Figure 14:
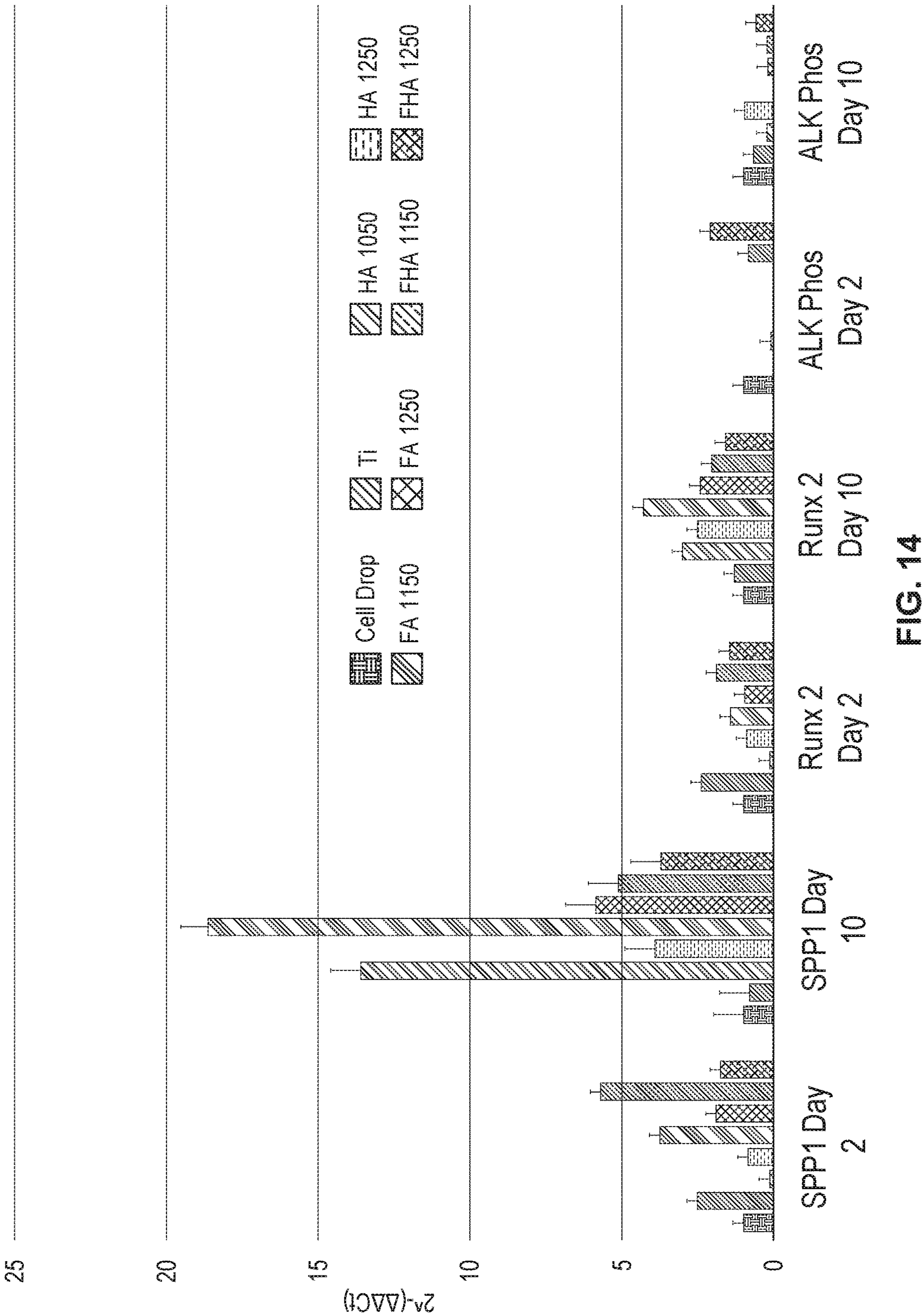
FIG. 14 is a bar graph of ΔΔct values of ADSCs plated on various samples.

FIG. 14 is a bar graph of ΔΔct values of ADSCs plated on various samples. All ΔΔct data is reported relative to cell drop control. At day two, apatite samples with the exception of HA 1150° C. and HA 1250° C. expressed more SPP1 than cell drop control ($p<0.01$) at. ADSCs seeded onto Ti and FHA 1250° C. had greater expression of all three osteogenic markers by day two. Cells plated onto the Ti surface exhibited greater levels of SPP1 (2.5±0.05; $p<0.01$) and Runx2 (2.3±0.05; $p<0.01$) compared to the cell drop control, but had undetectable levels of ALK Phos at two days post seeding. At day 2, HA 1150° C. had undetectable levels of SPP1, lower levels of the expression of Runx2 (0.06±0.07; $p<0.01$) and was not statistically different in terms of expression of ALK Phos (0.06±0.04; $p=0.38$) than cell drop control. SPP1 (0.9±0.05; $p=0.07$) and Runx 2 (0.9±0.07; $p=0.18$) expression in cells plated onto HA 1250° C. were not statistically different from cell drop control and ALK Phos was undetected. FA 1150° C. had much greater expression of SPP1 (4.1±0.05; $p<0.01$) and Runx2 (1.4±0.07; $p<0.01$) compared to cell drop control and undetectable levels of ALK Phos at two days. SPP1 expression was greater in cells seeded onto FA 1250° C. (1.8±0.05; $p<0.01$) but was not different in expression levels of Runx2 (0.96±0.07; $p=0.18$) and undetectable ALK Phos compared to cell drop control at two days. At two days, the FHA samples, both FHA 1150° C. and FHA 1250° C. has greater levels of SPP1 (5.7±0.05 and 1.8±0.05 respectively $p<0.01$) and Runx2 (1.8±0.07 and 1.4±0.07 respectively; $p<0.01$) compared to cell drop control. FHA 1150° C. (0.8±0.4, $p=0.8$) was not different than control and FHA 1250° C. (2.3±0.4, $p<0.5$) had greater expression than controls in terms of ADSC expression of ALK Phos at two days post seeding. According to FIG. 14, at two days, ADSCs seeded on both FA and FHA surfaces appeared to differentiate into a bone lineage to a greater extent than either HA formulations as exhibited by greater expression of SPP1 and Runx2 osteoblast markers.

On day two, protein expression of osteopontin (protein encoded by SPP1 gene) and osteocalcin were increased on FA 1250° C. pellets vs. HA 1250° C. pellets, suggesting preferential differentiation of ADSC lineage to an osteoblast phenotype with FA samples.

At day ten, there were no significant differences of levels of SPP1 ($p=0.8$), Runx2 ($p=0.5$), and ALK Phos ($p=0.07$) on Ti and cell drop control. Cells plated onto HA 1150° C. and HA 1250° C. had greater expression in measures of SPP1 (13.4±0.9 and 3.9±0.9 respectively; $p<0.01$) and Runx2 (3.0±0.2 and 2.5±0.2; $p<0.01$) at ten days. ALK Phos expression was lower on HA 1150° C. (0.2±0.1; $p<0.01$) but not on HA 1250° C. (1.0±0.1; $p=0.9$) compared to cell drop control at ten days. FA 1150° C. SPP1 (18.6±0.9; $p<0.01$) and Runx2 expression (4.3±0.2; $p<0.01$) was greater than the cell drop control, but ADSCs cells had undetectable levels of ALK Phos. Ten days post plating of ADSCs onto FA 1250° C. the cells expressed greater levels of both SPP1 (5.8±0.9; $p<0.01$) and Runx2 (2.4±0.2; $p<0.01$), but lower expression levels of ALK Phos (0.2±0.1; $p<0.01$). Similar to the cells plated onto FA 1250° C. ADSCs on FHA 1150° C. expressed greater levels of both SPP1 (5.0±0.9; $p<0.01$) and RUNX2 (2.0±0.2; $p<0.01$), and lower expression levels of ALK Phos (0.3±0.1; $p<0.01$) at ten days. ADSCs on FHA and cell drop control did not differ in SPP1 (3.6±0.9; $p=0.05$) and RUNX2 (1.6±0.2; $p=0.09$) expression levels, but did have lower expression of ALK Phos (0.6±0.1; $p<0.05$) at ten days.

While various aspects and embodiments have been disclosed herein, other aspects and embodiments are contemplated. The various aspects and embodiments disclosed herein are for purposes of illustration and are not intended to be limiting.

What is claimed is:

1. An implantable scaffold comprising:
- a scaffold structure, sized and shaped for implantation in an animal, and one or more bone growth dopants;
- wherein the scaffold structure consists of (i) fluorapatite, fluorohydroxyapatite, or a mixture thereof, and optionally, (ii) a binder and/or initiator; and
- wherein the scaffold structure exhibits a surface morphology and porosity consistent with having been sintered at 1150° C. to 1250° C.

2. The implantable scaffold of claim 1, further comprising a hydrogel coating, wherein the one or more bone growth dopants are disposed beneath the hydrogel coating.

3. The implantable scaffold of claim 2, wherein the hydrogel coating comprises keratose.

4. The implantable scaffold of claim 1, wherein the one or more bone growth dopants includes one or more of a differentiation promoter, stem cells, or demineralized bone matrix.

5. The implantable scaffold of claim 1, wherein the one or more bone growth dopants includes one or more of collagen, keratose, bone morphogenetic protein-2, adipose derived stem cells, or demineralized bone matrix.

6. The implantable scaffold of claim 1, wherein the one or more bone growth dopants include an autograft material.

7. The implantable scaffold of claim 1, wherein the surface morphology includes spherical, semi-spherical, prismatic, pseudo-prismatic, ellipsoid, or irregularly rounded fluoridated apatite particles that are devoid of rod-like or needle-like fluoridated apatite particles.

8. The implantable scaffold of claim 1, wherein fluoridated apatite of the fluoridated apatite structure exhibits a zeta potential of less than-10 mV.

9. The implantable scaffold of claim 1, wherein the implantable scaffold includes a bone implant, an osseointegrated implant, or a dental implant.

10. A method of making the implantable scaffold of claim 1, the method comprising:
- providing fluoridated apatite particles consisting of fluorapatite particles, fluorohydroxyapatite particles, or a mixture thereof, and optionally a binder and/or initiator;
- sintering the fluoridated apatite particles at a sintering temperature of 1150° C. to 1250° C. to form a sintered body; and
- forming the scaffold from the sintered body.

11. The method of claim 10, wherein providing fluoridated apatite particles includes providing fluorapatite particles with an average particles size between 60 μm to 200 μm.

12. The method of claim 10, wherein providing the fluoridated apatite particles includes casting the fluoridated apatite particles into a porous mold material.

13. The method of claim 10, further comprising doping the fluoridated apatite particles or the sintered body with one or more bone growth dopants.

14. A method of using the implantable scaffold of claim 1, the method comprising implanting the scaffold in a subject.

15. The method of claim 14, wherein implanting the scaffold includes one or more of sizing or shaping the scaffold.

16. The method of claim 14, further comprising adding one or more bone growth dopants to the scaffold.

* * * * *